US010444160B2

(12) United States Patent
Yang et al.

(10) Patent No.: US 10,444,160 B2
(45) Date of Patent: Oct. 15, 2019

(54) SURFACE DEFECTS EVALUATION SYSTEM AND METHOD FOR SPHERICAL OPTICAL COMPONENTS

(71) Applicant: ZHEJIANG UNIVERSITY, Hangzhou, Zhejiang (CN)

(72) Inventors: Yongying Yang, Zhejiang (CN); Dong Liu, Zhejiang (CN); Yang Li, Zhejiang (CN); Huiting Chai, Zhejiang (CN); Pin Cao, Zhejiang (CN); Fan Wu, Zhejiang (CN)

(73) Assignee: ZHEJIANG UNIVERSITY, Hangzhou, Zhejiang (CN)

( * ) Notice: Subject to any disclaimer, the term of this patent is extended or adjusted under 35 U.S.C. 154(b) by 0 days.

(21) Appl. No.: 15/509,159

(22) PCT Filed: Sep. 9, 2015

(86) PCT No.: PCT/CN2015/089217
§ 371 (c)(1),
(2) Date: Mar. 6, 2017

(87) PCT Pub. No.: WO2016/041456
PCT Pub. Date: Mar. 24, 2016

(65) Prior Publication Data
US 2017/0292916 A1  Oct. 12, 2017

(30) Foreign Application Priority Data

Sep. 18, 2014 (CN) .......................... 2014 1 0479580
Aug. 27, 2015 (CN) .......................... 2015 1 0535230
Aug. 27, 2015 (CN) .......................... 2015 1 0536104

(51) Int. Cl.
G01N 21/88  (2006.01)
G01N 21/958 (2006.01)
(Continued)

(52) U.S. Cl.
CPC ..... *G01N 21/8806* (2013.01); *G01M 11/0278* (2013.01); *G01N 21/8851* (2013.01);
(Continued)

(58) Field of Classification Search
CPC ... G01N 2021/8822; G01N 2021/9511; G01N 2021/9583; G01N 21/8806;
(Continued)

(56) References Cited

FOREIGN PATENT DOCUMENTS

CN    202229084 U   5/2012
CN    103293162 A   9/2013
(Continued)

Primary Examiner — Tri T Ton

(57) ABSTRACT

A defects evaluation system and method are provided in the present invention. Based on the principle of the microscopic scattering dark-field imaging, the present invention implements a sub-aperture scanning for the surface of spherical optical components and then obtains surface defects information with image processing. Firstly, the present invention takes full advantage of the characteristic that the surface defects of spherical optical components can generate scattering light when an annular illumination beam irradiates on the surface, to implement the sub-aperture scanning and imaging that covers the entire spherical surface. Then, a series of procedures such as the global correction of sub-apertures, the 3D stitching, the 2D projection and the digital feature extraction are taken to inspect spherical surface defects. Finally, actual size and position information of defects are evaluated quantitatively with the defects calibration data. The present invention achieves the automatic quantitative evaluation for surface defects of spherical optical components, which considerably enhance the efficiency and precision of the inspection, avoiding the influence of subjectivity on the results. Eventually, reliable numerical basis for the use and process of spherical optical components is provided.

20 Claims, 37 Drawing Sheets

(51) Int. Cl.
 *G01N 21/95* (2006.01)
 *G01M 11/02* (2006.01)
(52) U.S. Cl.
 CPC .......... *G01N 21/95* (2013.01); *G01N 21/958* (2013.01); *G01N 2021/8822* (2013.01); *G01N 2021/8887* (2013.01); *G01N 2021/9511* (2013.01); *G01N 2021/9583* (2013.01)
(58) Field of Classification Search
 CPC .. G01N 21/8851; G01N 21/958; G01N 21/88; G01N 21/952; G01N 21/956
 USPC ............... 356/239.1–239.8, 237.1–237.6
 See application file for complete search history.

(56) References Cited

FOREIGN PATENT DOCUMENTS

| | | |
|---|---|---|
| CN | 104215646 A | 12/2014 |
| CN | 204128987 U | 1/2015 |
| JP | 2013190252 A | 9/2013 |
| WO | 2010008303 A1 | 1/2010 |
| WO | 2010113232 A1 | 10/2010 |

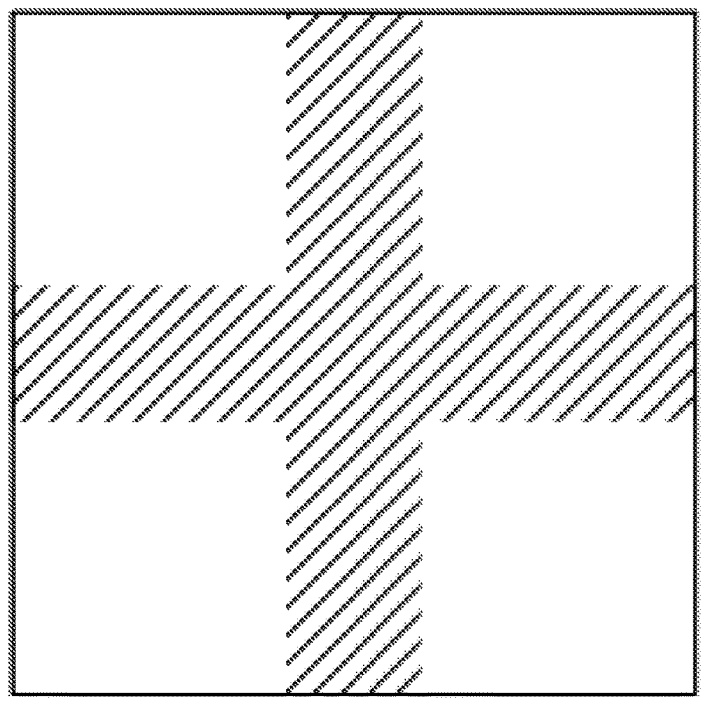
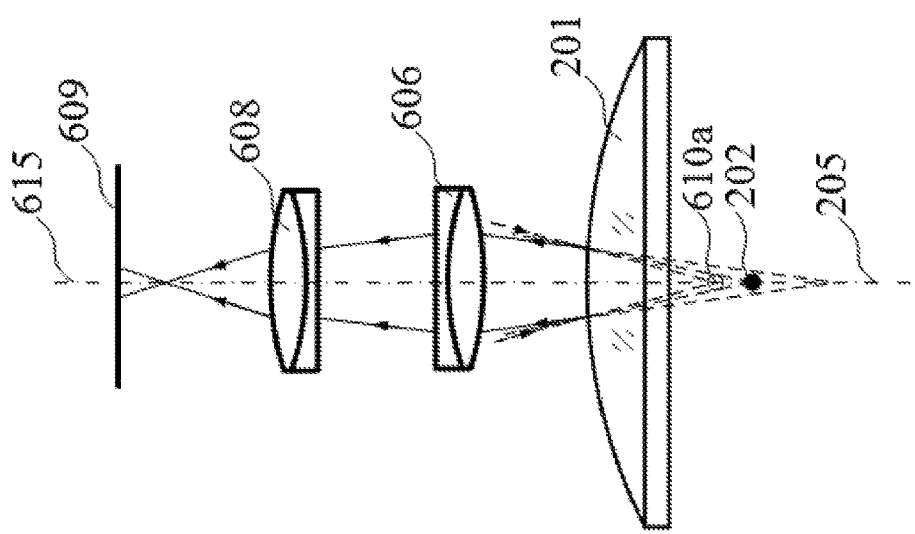
Fig 8B
Fig 8A

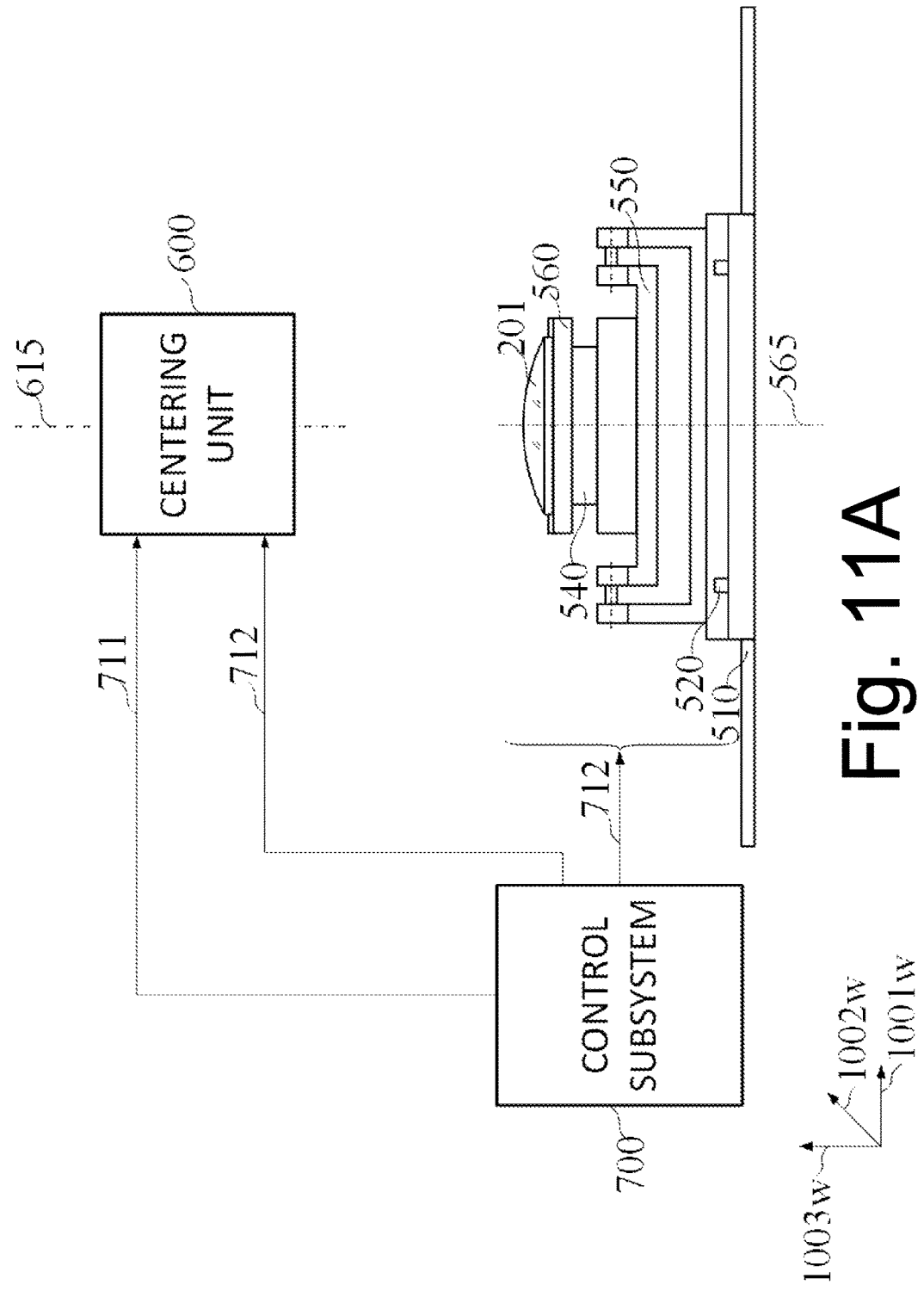

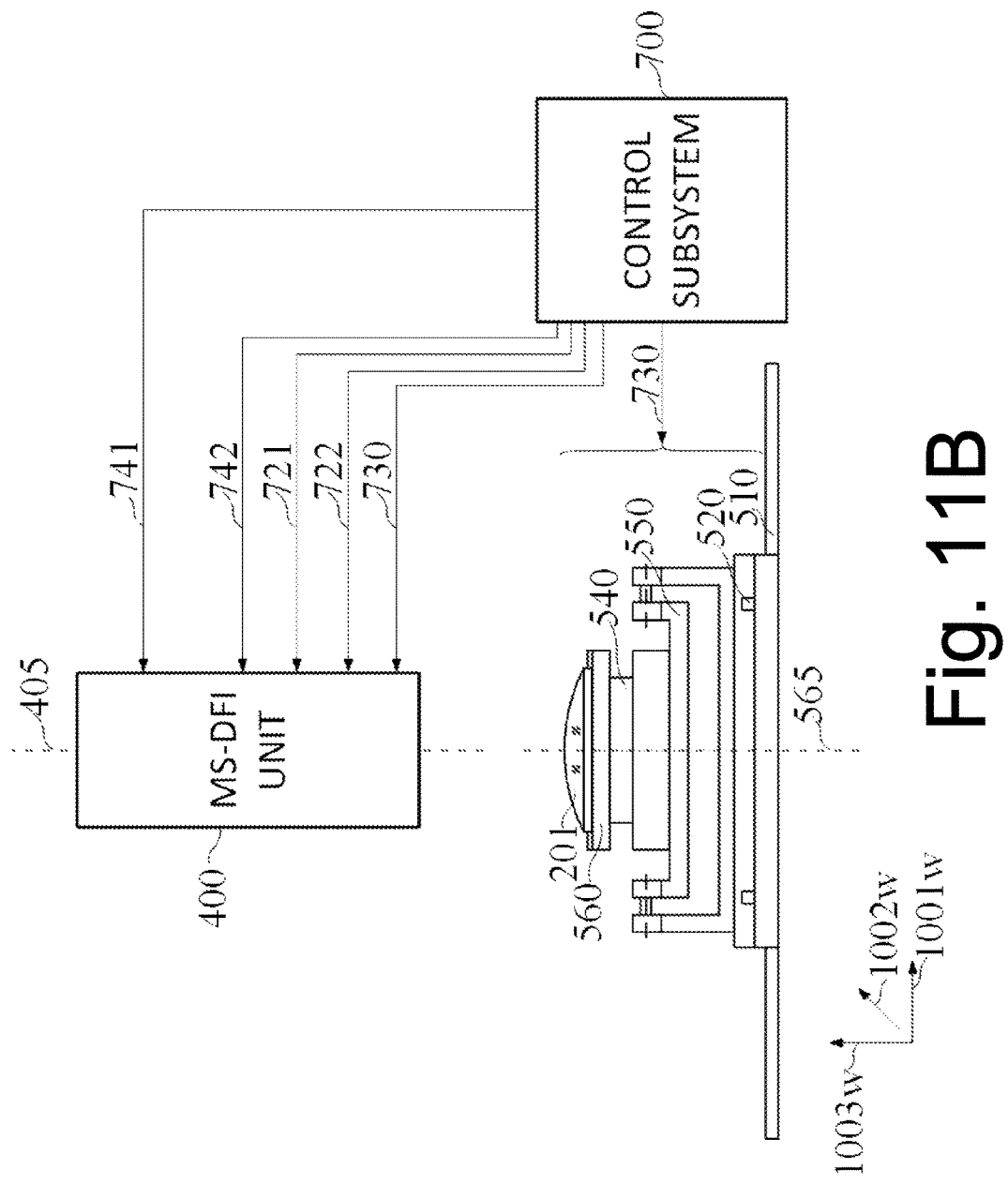

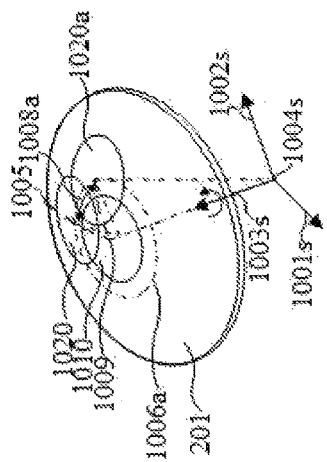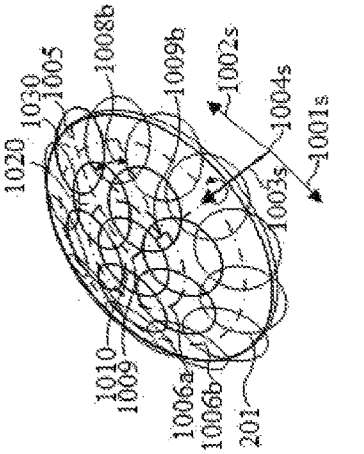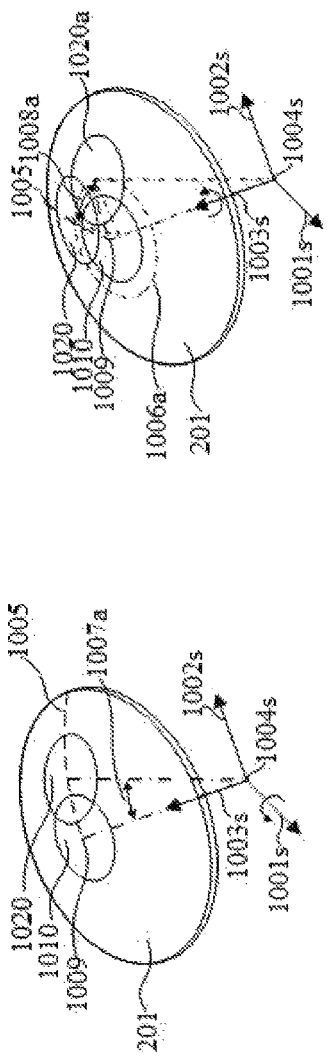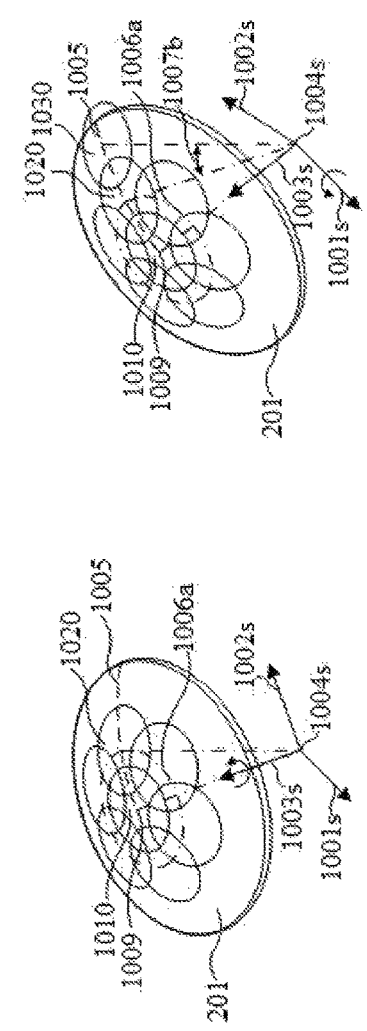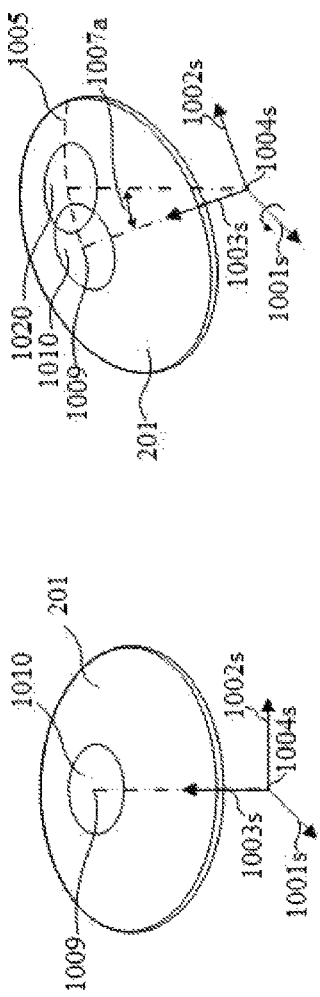
FIG. 14A  FIG. 14B  FIG. 14C  FIG. 14D  FIG. 14E  FIG. 14F

SURFACE DEFECTS EVALUATION SYSTEM AND METHOD FOR SPHERICAL OPTICAL COMPONENTS

CROSS REFERENCE OF RELATED APPLICATION

This is a U.S. National Stage under 35 U.S.C 371 of the International Application PCT/CN2015/089217, filed Sep. 9, 2015, which claims priority under 35 U.S.C. 119(a-d) to CN 201410479580.7, filed Oct. 18, 2014; CN 201510535230.2, filed Aug. 27, 2015; and CN 201510536104.9, filed Aug. 27, 2015.

BACKGROUND OF THE PRESENT INVENTION

Field of Invention

The present invention belongs to the technical field of machine vision inspection, relating to a defects evaluation system and method for spherical optical components.

Description of Related Arts

Spherical optical components are widely used in many optical systems including the large-aperture space telescope, the Inertial Confinement Fusion (ICF) system and the high-power laser system. However, defects such as scratches and digs on the surface of components can not only affect the imaging quality of optical systems, but also generate unnecessary scattering and diffraction light resulting in energy loss in the high-power laser system, which may also lead to a secondary damage because of the high energy. Therefore, it is highly necessary to inspect the surface defects of the spherical optical components before put into use and to digitally evaluate defects information to provide reliable numerical basis for the use of spherical optical components.

The traditional methods for inspecting the defects of spherical optical components are mostly based on the visual inspection. Using a strong light to illuminate the spherical surface, the inspector observes in different directions by naked eyes with the reflection method and the transmission method. However, the visual inspection suffers from subjectivity and uncertainty. It is greatly influenced by the proficiency of the inspector and can't provide quantitative description of defects information. Furthermore, a long-time inspection can cause eyes fatigue resulting in lower reliability. Accordingly, there remains a need for a system that can achieve the automatic evaluation for the surface defects on spherical optical components based on machine vision instead of manual visual method to considerably enhance the efficiency and precision of inspection.

SUMMARY OF THE PRESENT INVENTION

In allusion to the deficiencies of the existing technology, the present invention aims to provide an evaluation system and method to achieve the automatic inspection of the surface defects on spherical optical components.

Based on the principle of the microscopic scattering dark-field imaging, the present invention implements a sub-aperture scanning for the surface of spherical optical components and then obtains surface defects information with image processing. Firstly, the present invention takes full advantage of the characteristic that the surface defects of spherical optical components can generate scattering light when an annular illumination beam irradiates on the surface, to implement the sub-aperture scanning and imaging that covers the entire spherical surface. Then, a series of procedures such as the global correction of sub-apertures, the 3D stitching, the 2D projection and the digital feature extraction are taken to inspect spherical surface defects. Finally, actual size and position information of defects are evaluated quantitatively with the defects calibration data.

Spherical surface defects evaluation system (SSDES) comprises a defect imaging subsystem and a control subsystem. The defect imaging subsystem is adapted to acquire microscopic scattering dark-field images suitable for digital image processing. The control subsystem is adapted to drive the movements of various parts of the defect imaging subsystem, to realize automatic scanning and inspection of defects on the spherical surface. The defect imaging subsystem comprises an illumination unit, a microscopic scattering dark-field imaging (MS-DFI) unit, a spatial position and posture adjustment (SPPA) unit and a centering unit. The illumination unit is adapted to provide dark-field illumination for microscopic scattering dark-field imaging of spherical surface. The MS-DFI unit is adapted to collect scatter light induced by the surface and image. The SPPA unit is adapted to achieve five-dimensional spatial position and attitude adjustment including three-dimensional translation, rotation and swing, easy to acquire sharp images at various locations on the surface of the spherical optical component. The centering unit is adapted to analyze the position of the curvature center of the component. The movement and the adjustment of the illumination unit, the MS-DFI unit, the SPPA unit and the centering unit are driven by the control subsystem.

The illumination unit comprises illuminants and an illuminant support bracket. The illuminant comprises a uniform surface light source and a lens group with front fixed lens group, zoom lens group and rear fixed lens group installed in. The optical axis of the lens group intersects with the optical axis of the MS-DFI unit at the incident angle of γ ranging from 25 to 45 degrees.

The illuminant support bracket comprises a top fixation board, a hollow shaft, a worm gear, a worm, a servo motor, a motor support, bearings, a rotating cylindrical part and illuminant fixation supports. The illuminant is fixed on the illuminant support bracket which is fixed on the rotating cylindrical part. The rotating cylindrical part has flexible connections with the hollow shaft by the bearings. The worm gear, installed on the rotating cylindrical part has flexible connections with the worm and achieve circular rotation by the drive of the servo motor. The servo motor is fixed on the top fixation board by the motor support and the hollow shaft is also fixed on the top fixation board, which is fixed on the Z-axis translation stage. The illuminant support bracket is applied to provide illumination for spherical surface defects in all directions.

Three illuminants are in annular and uniform distribution at the angle interval of 120° by the illuminant fixation support on the rotating cylindrical part.

The light path of the illumination unit is formed as follows. The zoom lens group is moved to the position in the lens group calculated according to the curvature radius of the spherical optical component. The parallel light emitted by the uniform surface light source enters into the lens group and passes through the front fixed lens group, the zoom lens group and the rear zoom lens group in turn. Finally it becomes convergent spherical wave with the aperture angle of $\theta_I$.

Taking advantages of the induced scatter light by the principle that defects on the smooth surface modulate the incident light, the MS-DFI unit achieves microscopic dark-field imaging of defects and acquires dark-field images of defects. The principle is as follows. The incident light is incident onto the surface of the spherical optical component. If the spherical surface is smooth, the incident light, according to the law of reflection in geometrical optics, is reflected on the surface to form the reflected light, which can't enter the MS-DFI unit. If there is defect on the surface of the spherical optical component, the incident light is scattered to form the scatter light, which is received by the MS-DFI unit and forms the dark-field image of defects.

The SPPA unit comprises an X-axis translation stage, a Y-axis translation stage, a Z-axis translation stage, a rotation stage, a swing stage and a self-centering clamp. The swing stage comprises an inner plate and a shell plate. The self-centering clamp has fixed connections with the rotation axis of the rotation stage and the base of the rotation stage is fixed on the inner plate of the swing stage. The inner plate has flexible connections with the shell plate so that the inner plate is capable of swinging by the shell plate. The sections of the inner plate and the shell plate are both in U-shape. The undersurface of the shell plate of the swing stage is fixed on the working surface of the Y-axis translation stage and the Y-axis translation stage is fixed on the working surface of the X-axis translation stage. The X-axis translation stage and the Z-axis translation stage are fixed on the same platform.

The centering unit comprises a light source, a focusing lens group, a reticle, a collimation lens, a beam splitter, an objective, a plane reflector, an imaging lens and a CCD. The light beam emitted by the light source passes through the focusing lens group and irradiates the reticle with a crosshair on. Then, the light beam passes through the collimation lens, the beam splitter and the objective and irradiates on the spherical optical component. The light beam is reflected on the surface and the image of the crosshair on the reticle is indicated by the reticle image. The reflected light beam passes through the objective again and deflects at the beam splitter. Subsequently, the reflected light beam is reflected by the plane reflector and passes through the imaging lens. Finally, the light beam focuses on the CCD and the CCD acquires the image of the crosshair on the reticle.

The control subsystem comprises a centering control module, an illumination control module, a five-stage translation control module and an image acquisition control module. The centering control module comprises a centering image acquisition unit and a four-stage translation control unit. The centering image acquisition unit is applied to control the CCD of the centering unit to acquire the image of the crosshair and the four-stage translation control unit is applied to control the movement of the X-axis translation stage, the Y-axis translation stage and the Z-axis translation stage and the rotation of the rotation stage during the process of centering. The illumination control module comprises an illumination rotating control unit and an illuminant zoom control unit. The illumination rotating control unit is applied to control the rotation of the illuminant support bracket of the illumination unit and the illuminant zoom control unit is applied to control the movement of the zoom lens group to change the aperture angle $\theta_i$ of the emitted convergent spherical wave. The five-stage translation control module is applied to control the movement of the X-axis translation stage, the Y-axis translation stage and the Z-axis translation stage, the rotation of the rotation stage and the swing of the swing stage during the process of inspection. The image acquisition control module comprises a sub-aperture image acquisition unit and a microscope zoom control unit. The sub-aperture image acquisition unit is applied to control the MS-DFI unit to acquire sub-aperture images and the microscope zoom control unit is applied to change the image magnification of the MS-DFI unit.

The evaluation method comprises an automatic centering module, a scan-path planning module, an image processing module and a defect calibration module. The automatic centering module is adapted to automatic centering of the spherical surface, achieving accurate measurement of the curvature radius and axial consistency alignment between the rotation axis and the optical axis of the spherical optical component. The scan-path planning module is adapted to plan the optimal scan-path for the spherical surface. The image processing module is adapted to achieve spherical surface defects inspection with high precision. The defect calibration module is adapted to establish the relationship between pixels and actual size in sub-aperture images at any locations on the spherical surface in order that the actual size of defects can be obtained. The evaluation method comprises the following steps:

Step1. The implementation of automatic centering of the spherical optical component by the automatic centering module.

Step2. The completion of optimal scan-path planning and full-aperture scanning for the spherical optical component by the scan-path planning module.

Step3. The obtainment of spherical surface defect information by the image processing module and the defect calibration module.

The implementation of automatic centering of the spherical surface by the automatic centering module according to Step 1, comprises the following steps:

1-1. Initialize the centering unit.

1-2. Move the spherical optical component to the initial position where the optical axis of the spherical optical component coincides with the optical axis of the centering unit approximately.

1-3. The Z-axis translation stage is controlled to scan along Z-direction to find the sharpest crosshair image by use of image entropy clarity evaluation function.

1-4. Judge whether the crosshair image is the surface image or the center image as follows:

Move the X-axis translation stage and Y-axis translation stage slighted to observe whether the crosshair image in the field of view (FOV) is moved with the movement of translation stages or not. If the crosshair image is moved with the movement of stages, it is the center image of the spherical optical component located at the curvature center of the spherical optical component and then jump to Step 1-5. Otherwise, it is the surface image of the spherical optical component located on the surface of the spherical optical component and then jump to Step 1-9.

1-5. Move the crosshair image to the center of FOV by the X-axis translation stage and the Y-axis translation stage. After the movement, the optical axis of the spherical optical component coincides with the optical axis of the centering unit.

1-6. Find the position of the rotation axis by rotation measurement in optical alignment as follows:

The spherical optical component can rotate around the rotation axis of the rotation stage under the self-centering clamp. Every 30° rotation of the rotation stage, CCD acquires a crosshair image. The positions of the crosshair images in the FOV of CCD vary with different rotation angles. The trajectory formed by the center of the crosshair is close to a circle, the center of which is the position of the rotation axis.

1-7. Obtain the trajectory center by the least square circle fitting method and the max deviation between the trajectory center and the crosshair center is calculated.

1-8. Judge whether the max deviation is lower than the max permissible error. If the max deviation is lower than the max permissible error, the axial consistency alignment is considered completed. Otherwise, the optical axis of the spherical optical component is not coincident with the rotation axis, therefore the center of the crosshair image is moved to the fitting trajectory center by adjusting the self-centering clamp and then jump to Step 1-5.

1-9. Move the Z-axis translation stage to image at theoretical curvature center obtained by initialization. The Z-axis translation stage is controlled to scan along Z-direction to find the sharpest crosshair image and then jump to Step 1-5. At the same time, Z-direction displacement from the position of the surface image to the position of the center image is recorded to get the real curvature radius of the spherical optical component, which is the displacement of the Z-axis translation stage.

The completion of optimal scan-path planning and full-aperture scanning for the spherical optical component by the scan-path planning module according to Step 2, comprises the following steps:

2-1. With the fiducial position obtained in the process of axial consistency alignment in Step 1, the spherical optical component is moved by the SSPA unit below the MS-DFI unit. Then the MS-DFI unit acquires the sub-aperture located at the vertex of the spherical surface. For the convenience of the following statement, spherical coordinate system $X_s Y_s Z_s$ is defined here, whose origin $O_s$ is located at the curvature center of the spherical optical component and z-axis $Z_s$ passes through the vertex of the spherical surface. To achieve the full-aperture sampling, two-dimension movements along the meridian and parallel scanning trajectory is required, combining the swing around $X_s$ and the rotation around $Z_s$.

2-2. The spherical optical component is driven to swing around $X_s$ with swing angle $\beta_1$, one sub-aperture image is acquired on the meridian. After that, rotating around $Z_s$ with rotation angle $\alpha_1$ is implemented to acquire another sub-aperture image on the parallel.

2-3. Every time after the rotation around $Z_s$ with the same rotation angle $\alpha_1$, one sub-aperture is acquired so that multiple sub-apertures on the parallel are obtained.

2-4. After the completion of sub-aperture acquisition on the parallel, the spherical optical component is driven to swing around $X_s$ again with swing angle $\beta_2$, then one sub-aperture is acquired on meridian.

2-5. Every time after the rotation around $Z_s$ with the same rotation angle $\alpha_2$, one sub-aperture is acquired so that multiple sub-apertures on the parallel are obtained. Full-aperture sampling is finished with several times repetition of such a process that the spherical optical component is driven to swing around $X_s$ with swing angle $\beta_2$ to acquire multiple sub-apertures on next parallel after the completion of sub-aperture acquisition on this parallel.

According to Step 2, the completion of optimal scan-path planning and full-aperture scanning for the spherical optical component by the scan-path planning module is characterized by that the sub-aperture plan model is established firstly. In this model, sub-aperture A and sub-aperture B are two adjacent sub-apertures on meridian C. Sub-aperture Aa is adjacent to sub-aperture A on parallel D1 where sub-aperture A is located. Similarly, sub-aperture Bb is adjacent to sub-aperture B on parallel D2 where sub-aperture B is located. Besides, the bottom intersection of sub-aperture A and sub-aperture Aa is indicated by $P_{cd}$, the top intersection of sub-aperture B and sub-aperture Bb is indicated by $P_{cu}$. So the sufficient conditions for the realization of sub-aperture no-leak inspection is that the arc length $\overparen{P_{cu}O_f}$ is less than or equal to the arc length $\overparen{P_{cd}O_{f'}}$. Under such a constraint, planning result can be solved and obtained by establishing the relationship between swing angle $\beta_1$, swing angle $\beta_2$ and rotation angle $\alpha_1$, rotation angle $\alpha_2$. The solution procedure of swing angle $\beta_1$, swing angle $\beta_2$, rotation angle $\alpha_1$ and rotation angle $\alpha_2$ is as follows:

①  Validate relevant parameters about the spherical optical component, including the curvature radius, aperture of the spherical optical component and the size of the object field of view of the MS-DFI unit.

②  Specify the initial value of swing angle $\beta_1$ and swing angle $\beta_2$ according to the above three parameters. After that, calculate the value of rotation angle $\alpha_1$ and rotation angle $\alpha_2$ according to the same overlapping area between adjacent sub-apertures on one parallel. Then, figure out arc length $\overparen{P_{cu}O_f}$ and arc length $\overparen{P_{cd}O_{f'}}$.

③  Compare arc length $\overparen{P_{cu}O_f}$ and arc length $\overparen{P_{cd}O_{f'}}$ to determine whether the given initial value of swing angle $\beta_2$ is appropriate or not. If $\overparen{P_{cu}O_f} > \overparen{P_{cd}O_{f'}}$, reduce the value of swing angle $\beta_2$ by 5% and go back to Step ②. Otherwise, sub-aperture plan for covering the entire spherical surface is finished.

The obtainment of spherical surface defects information by the image processing module and the defect calibration module according to Step 3, comprises the following steps:

3-1. The imaging sub-aperture image is a2D image, which is obtained when the surface of the spherical optical component is imaged by the MS-DFI unit in the image plane. Due to the information loss along the direction of optical axis during the optical imaging process, 3D correction of sub-apertures should be conducted firstly to recover the information loss of surface defects of the spherical optical component along the direction of optical axis during the optical imaging process. 3D correction of sub-apertures means that the imaging process of the MS-DFI unit is simplified to be a pin-hole model and imaging sub-aperture images are transformed into 3D sub-aperture images with geometrical relationship.

3-2. For convenience of feature extraction, 3D sub-aperture images obtained after 3D correction of sub-apertures are projected onto a 2D plane with full-aperture projection to obtain the full-aperture projective image.

3-3. Feature extraction at low magnification is conducted on the full-aperture projective image; then 3D sizes of defects is obtained with inverse-projection reconstruction; finally, actual sizes and positions of surface defects on the spherical optical component are obtained taking advantages of the defect calibration data got with the calibration module.

3-4. Defects are inspected at high magnification to guarantee the micron-scale inspection precision. First, the imaging magnification of the MS-DFI unit is zoomed to high magnification; then, according to the positions obtained by Step 3-3, surface defects are moved to the center of the object field of view to acquire images at high magnification; Finally, feature extraction at high magnification is conducted and micron-scale evaluation results of defects are obtained taking advantages of the defect calibration data got with the calibration module.

3-5. Evaluation results are output in the form of 3D panoramic preview of the spherical surface, electronic report and defect location map.

According to Step 3-1, imaging sub-aperture images are obtained when the surface of the spherical optical component is imaged by the MS-DFI unit in the image plane. The detailed description is as follows:

3-1-1. According to the optimal scan-path planned by the scan-path planning module in Step 2, one point p on the surface of the spherical optical component is moved to the point p' by the SPPA unit.

3-1-2. The MS-DFI unit acquires sub-apertures at low magnification. Point p' is imaged to be image point p" in the imaging sub-aperture image by the MS-DFI unit.

3-1-3. During the process of digital image acquisition, the image-plane coordinate system $X_c Y_c$ is transformed into the image coordinate system $X_i Y_i$ and the imaging sub-aperture image is obtained. X-axis $X_c$ and y-axis $Y_c$ compose the image-plane coordinate system $X_c Y_c$, whose origin $O_c$ is located at the intersection of the optical axis of the MS-DFI unit and the imaging sub-aperture image. X-axis $X_i$ and y-axis $Y_i$ compose the image coordinate system $X_i Y_i$ coordinate system, whose origin $O_i$ is located at the top left corner of the digital image.

According to Step 3-2, the full-aperture projective image is obtained. The detailed description is as follows:

3-2-1. 3D sub-aperture images are transformed into spherical sub-aperture images by global coordinate transformation.

3-2-2. Spherical sub-aperture images are projected vertically onto the plane to obtain projective sub-aperture images.

3-2-3. Projective sub-aperture images are stitched and sizes and positions of defects are extracted in the plane. Precise inspection for surface defects of the spherical optical component can be achieved by inverse-projection reconstruction. The way of direct stitching for parallel circle and annulus stitching for meridian circle is used for image stitching of projective sub-aperture images. The process of image stitching of projective sub-aperture images is as follows:

① Projective sub-aperture images are denoised to remove the effect of background noise on stitching accuracy.

② After denoising, image registration according to overlapping area is carried out on adjacent projective sub-aperture images on the same parallel circle.

③ Adjacent projective sub-aperture images after registration on the same parallel circle are stitched to obtain the annulus image of one parallel circle.

④ The minimum annulus image containing all overlapping areas is extracted.

⑤ The image registration points of the minimum annulus image are extracted to acquire the best registration location, so that the image stitching of projective sub-aperture images is finished.

According to Step 3-3, feature extraction at low magnification is conducted on the full-aperture projective image; then, 3D sizes of defects is obtained with inverse-projection reconstruction; finally, actual sizes and positions of surface defects of the spherical optical component are obtained taking advantages of the defect calibration data got with the defect calibration module. The detailed description is as follows:

3-3-1. Extract features of the 2D full-aperture image after image stitching of projective sub-aperture images to obtain sizes and positions of defects.

3-3-2. Obtain 3D sizes and positions in pixels of surface defects of the spherical optical component by inverse-projection reconstruction.

3-3-3. Taking advantages of the defect calibration data got with the defect calibration module, convert 3D sizes and positions in pixels to actual sizes and positions.

The defect calibration data according to Step 3-3 and Step 3-4 comprises defect length calibration data and defect width calibration data. The process of defect length calibration is to establish the relationship between actual lengths of line segments at any locations on the spherical surface and corresponding pixels in spherical sub-aperture images. The defect length calibration data is obtained as follows:

Firstly, a standard line segment $d_l$ is taken in the object plane and its length is measured by a standard measuring instrument. Standard line segment $d_l$ is imaged by the MS-DFI unit and its image $d_p$ can be obtained in the imaging sub-aperture image.

Then, this imaging sub-aperture image is transformed into a 3D sub-aperture image by 3D correction, in which the spherical image of standard line segment $d_l$, namely a short arc $d_c$ on the spherical surface can be obtained. The size of $d_c$ is quantified in pixels and its corresponding arc angle $d_\theta$ is obtained. Since the curvature radius R of the spherical optical component can be determined accurately during the process of centering, the corresponding actual size of $d_c$ can be deduced by $d=Rd_\theta$. By establishing the relationship between $d_c$ and d, the relationship between the pixels in the 3D sub-aperture image and the actual size is calibrated, namely the calibration coefficient $k=d/d_c$. If substituting the equation $d=Rd_\theta$, we have $k=Rd_\theta/d_c$. Continuing to substitute the equation $d_c=R_{pixel}d_\theta$, we can finally deduce calibration coefficient by $k=R/R_{pixel}$, where $R_{pixel}$ is the curvature radius in pixels of the 3D spherical surface image, called pixel curvature radius for short. To extract the length of surface defects on one spherical optical component, feature extraction is firstly implemented to get each pixel's position coordinates of defects. Then the continuous defects are discretized into a plurality of line segments described by a series of line equations $l_i$: $y_i=k_ix_i+b_i$ based on position coordinates, where i=1, 2, 3 . . . n. After the process of inverse-projection reconstruction for each line segment, the corresponding arc $C_i$ of line segment $l_i$ on the spherical surface with the curvature radius $R_{pixel}$ is obtained. And the length of defects in pixels can be figured out with the surface integral equation:

$$L_{pixel} = \sum_{i=1}^{n} \left( \int_{C_i} ds \right)$$

where ds refers to the curve differential element. After substituting the calibration coefficient k, the actual length of defects can be obtained by:

$$L_{real} = \sum_{i=1}^{n} k_i \left( \int_{C_i} ds \right)$$

The defect width calibration data is obtained as follows:

Firstly, in the 3D coordinate system, a standard line segment is taken in the object plane and its actual width is measured by a standard measuring instruments. The standard line segment is imaged by the MS-DFI unit and its image can be obtained in the imaging sub-aperture image.

Then, this imaging sub-aperture image is transformed into a 3D sub-aperture image by 3D correction, in which the spherical image of the standard line segment can be obtained. For the spherical image, the arc length in pixels along width direction is the width of defects in pixels. Since the defects are located in the center of FOV during the process of image acquisition at high magnification, information loss along the direction of the optical axis can be ignored. Thus, the actual width of defects is equal to that of the standard line segment.

Finally, a piecewise fitting for the corresponding discrete points of actual width and width in pixels of defects is used to obtain the best fitting curve, which is as the calibration transfer function (CTF). With the CTF, the actual width at any locations on the spherical surface can be calculated from the width in pixels.

The present invention achieves the automatic quantitative evaluation for surface defects of spherical optical components, which not only liberates the inspectors from the heavy work of visual inspection, but also considerably enhance the efficiency and precision of the inspection, avoiding the influence of subjectivity on the results. Eventually, reliable numerical basis for the use and process of spherical optical components is provided.

BRIEF DESCRIPTION OF THE DRAWINGS

FIG. 1 illustrates a block diagram of surface defects evaluation system and method for spherical optical components in accordance with the first and the second embodiment of the present invention;

FIG. 8A illustrates a schematic diagram of the light path in the case of Z-direction deviation between the positions of the reticle image and the curvature center of the convex spherical optical component in accordance with FIG. 7;

FIG. 8B illustrates an image of the crosshair captured by CCD in the case of Z-direction deviation between the positions of the reticle image and the curvature center of the spherical optical component in accordance with FIG. 7;

FIG. 11A illustrates a schematic diagram of portions of the control subsystem when SSDES operates in centering mode in accordance with FIG. 10;

FIG. 11B illustrates a schematic diagram of portions of the control subsystem when SSDES operates in inspection mode in accordance with FIG. 10;

FIG. 14 illustrates a schematic diagram of sub-aperture scanning in accordance with FIG. 1;

FIG. 14(a) illustrates a schematic diagram of acquiring sub-aperture located at the vertex of the spherical surface.

FIG. 14(b) illustrates a schematic diagram that the convex spherical optical component swings with an angle to begin acquiring sub-apertures on the first parallel.

FIG. 14(c) illustrates a schematic diagram of acquiring other sub-apertures on the first parallel by rotation.

FIG. 14(d) illustrates a schematic diagram of obtaining multiple sub-apertures on the first parallel.

FIG. 14(e) illustrates a schematic diagram that the convex spherical optical component swings with an angle to begin acquiring sub-apertures on the second parallel.

FIG. 14(f) illustrates a schematic diagram of obtaining multiple sub-apertures on the second parallel.

DETAILED DESCRIPTION OF THE PREFERRED EMBODIMENT

Hereinafter, the present invention will now be described in detail with the combination of the accompany drawings and the embodiments.

The present invention is capable to evaluate the surface defects of both convex and concave spherical optical components. The first embodiment applies to the surface defects evaluation of the convex spherical optical components. The second embodiment applies to the surface defects evaluation of the concave spherical optical components. The third embodiment applies to the surface defects evaluation of the small-aperture spherical optical component. In this case, the evaluation method is much more simplified because only single sub-aperture image is required to obtain dark-field image covering the full-aperture.

Embodiments of the present invention will be described in detail with reference to the above drawings. In principle, the same components are indicated by the same reference numbers in all drawings for describing the embodiments.

First Embodiment

Hereafter, a first embodiment of the present invention will be described in detail with reference to FIGS. 1 to 25, which describes surface defects evaluation system and method for convex spherical optical components.

Figure 1:
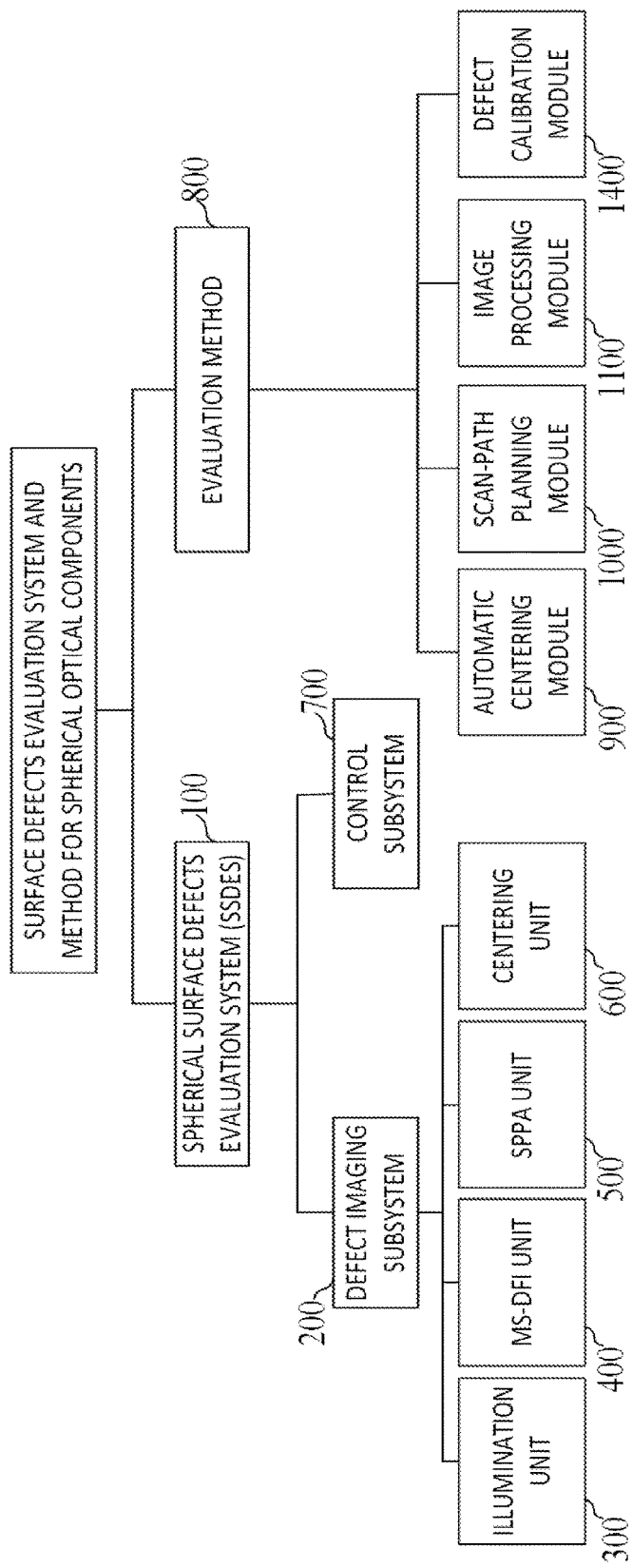
FIG. 1 is a perspective view of according to a preferred embodiment of the present invention.

FIG. 1 illustrates a block diagram of surface defects evaluation system and method for spherical optical components in accordance with the first and the second embodiment of the present invention. The SSDES 100 comprises a defect imaging subsystem 200, a control subsystem 700. The defect imaging subsystem 200 is adapted to acquire microscopic scattering dark-field images suitable for digital image processing. The control subsystem 700 drives the movements of the illumination unit 300, the MS-DFI unit 400, the SPPA unit 500 and the centering unit 600, to acquire images of the inspected surface of the spherical optical component.

Referring to FIG. 1, the defect imaging subsystem 200 comprises an illumination unit 300, an MS-DFI unit 400, a SPPA unit 500 and a centering unit 600. The illumination unit 300 is adapted to provide dark-field illumination for the MS-DFI unit 400. The MS-DFI unit 400 is adapted to collect scatter light induced by the surface and image. The SPPA unit 500 is adapted to achieve five-dimensional spatial position and attitude adjustment including three-dimensional translation, rotation and swing, easy to acquire sharp images at various locations on the surface of the spherical optical component. The centering unit 600 is adapted to analyze the position of the curvature center of the component. The movement and the adjustment of the illumination unit 300, the MS-DFI unit 400, the SPPA unit 500 and the centering unit 600 are driven by the control subsystem 700.

The illumination unit 300 is adapted to provide dark-field illumination for the MS-DFI unit 400. Common parallel light source is not suitable for dark-field illumination because the incident light that doesn't pass through the curvature center of the component is reflected by the spherical surface, passes through the MS-DFI unit 400 and becomes a bright-field reflective spot finally, destroying the dark-field illumination condition. Therefore, the illumination unit 300, which is provided for surface defects inspection for spherical optical components, emits illumination light with the aperture angle varying with the curvature radiuses, providing dark-field illumination for the convex spherical optical component.

Figure 3:
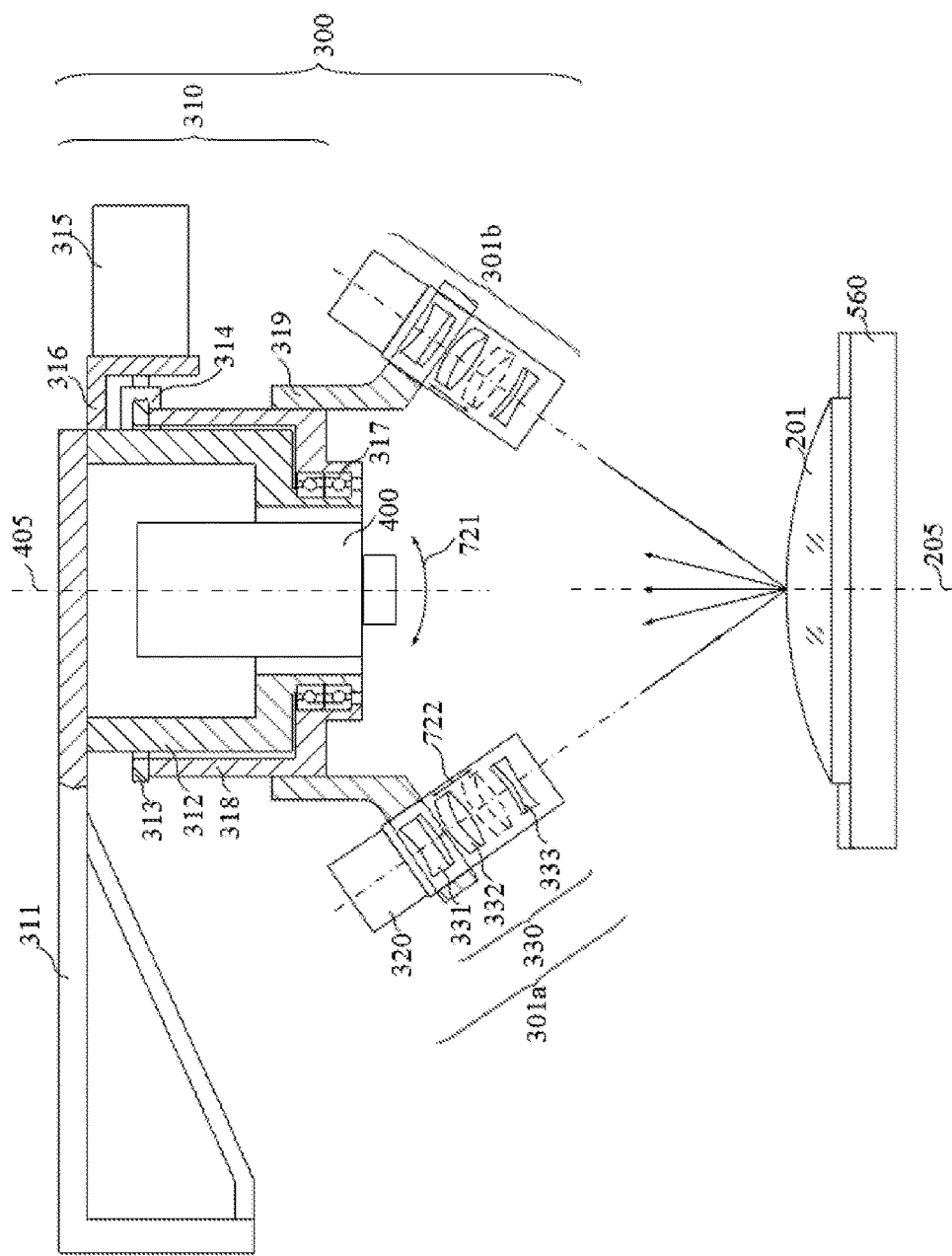
FIG. 3 illustrates a schematic diagram of the structure of the illumination unit in accordance with FIG. 1.

FIG. 3 illustrates a schematic diagram of the structure of the illumination unit 300 in accordance with FIG. 1. The illumination unit 300 comprises illuminants and an illuminant support bracket 310. The illuminant comprises a uniform surface light source 320 and a lens group 330 with front fixed lens group 331, zoom lens group 332 and rear fixed lens group 333 installed in. The optical axis of the lens group 330 intersects with the optical axis of the MS-DFI unit 405 at the incident angle of γ ranging from 25 to 45 degrees.

The illuminant support bracket 310 comprises a top fixation board 311 a hollow shaft 312, a worm gear 313, a worm 314, a servo motor 315, a motor support 316, bearings 317, a rotating cylindrical part 318 and illuminant fixation supports 319. The illuminant is fixed on the illuminant support bracket 319 which is fixed on the rotating cylindrical part 318. The rotating cylindrical part 318 has flexible connections with the hollow shaft 312 by the bearings 317. The worm gear 313, installed on the rotating cylindrical part 318 has flexible connections with the worm 314 and achieve circular rotation by the drive of the servo motor 315. The servo motor 315 is fixed on the top fixation board 311 by the motor support 316 and the hollow shaft 312 is also fixed on the top fixation board 311, which is fixed on the Z-axis translation stage 530.

The illuminant support bracket 310 is applied to provide illumination for spherical surface defects in all directions. Three illuminants 301a, 301b and 301c are in annular and uniform distribution at the angle interval of 120° by the illuminant fixation support 319 on the rotating cylindrical part 318. The servo motor 315 is driven by the illumination rotating control module 721 to achieve annular illumination.

Figure 4:
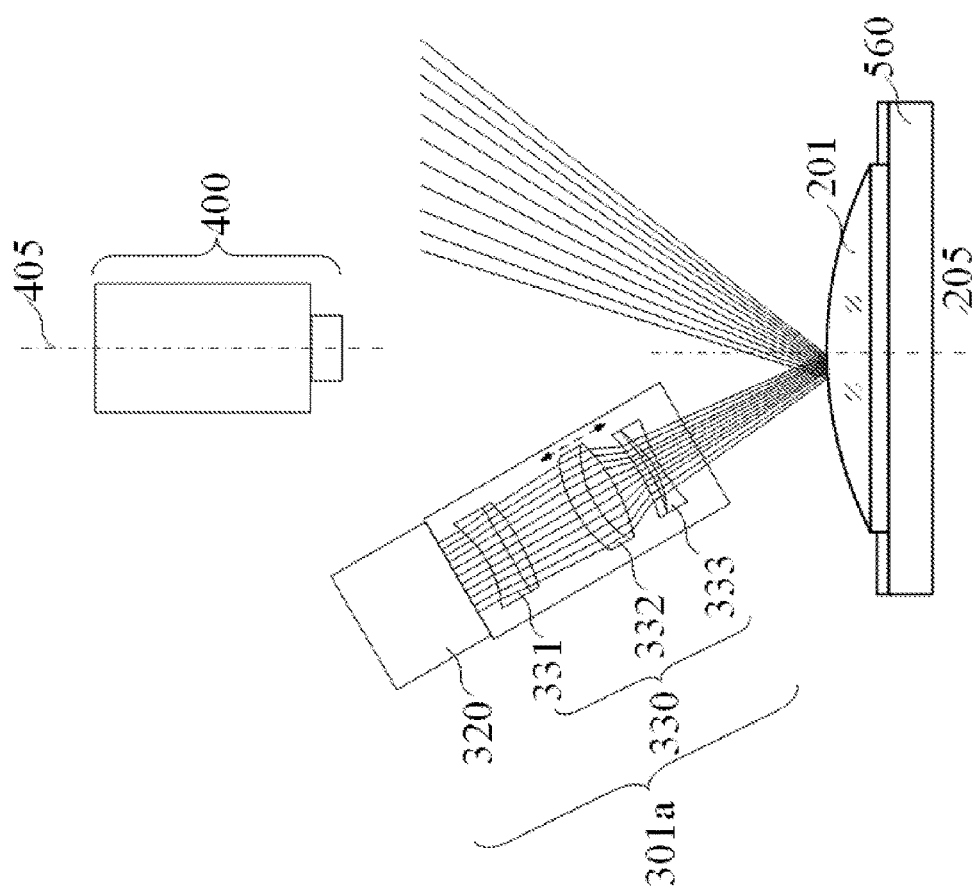
FIG. 4 illustrates a schematic diagram of the illumination light path in accordance with the first embodiment of the present invention.

FIG. 4 illustrates a schematic diagram of the illumination light path in accordance with the first embodiment of the present invention. The parallel light emitted by the uniform surface light source 320 passes through the lens group 330 and becomes convergent spherical wave with the aperture angle of $\theta_l$. The detailed process is as follows. The zoom lens group 332 is moved to the position in the lens group 330 calculated according to the curvature radius of the convex spherical optical component 201. The parallel light emitted by the uniform surface light source 320 enters into the lens group 330 and passes through the front fixed lens group 331, the zoom lens group 332 and the rear zoom lens group 333 in turn. Finally it becomes convergent spherical wave with the aperture angle of $\theta_l$.

Figure 5:
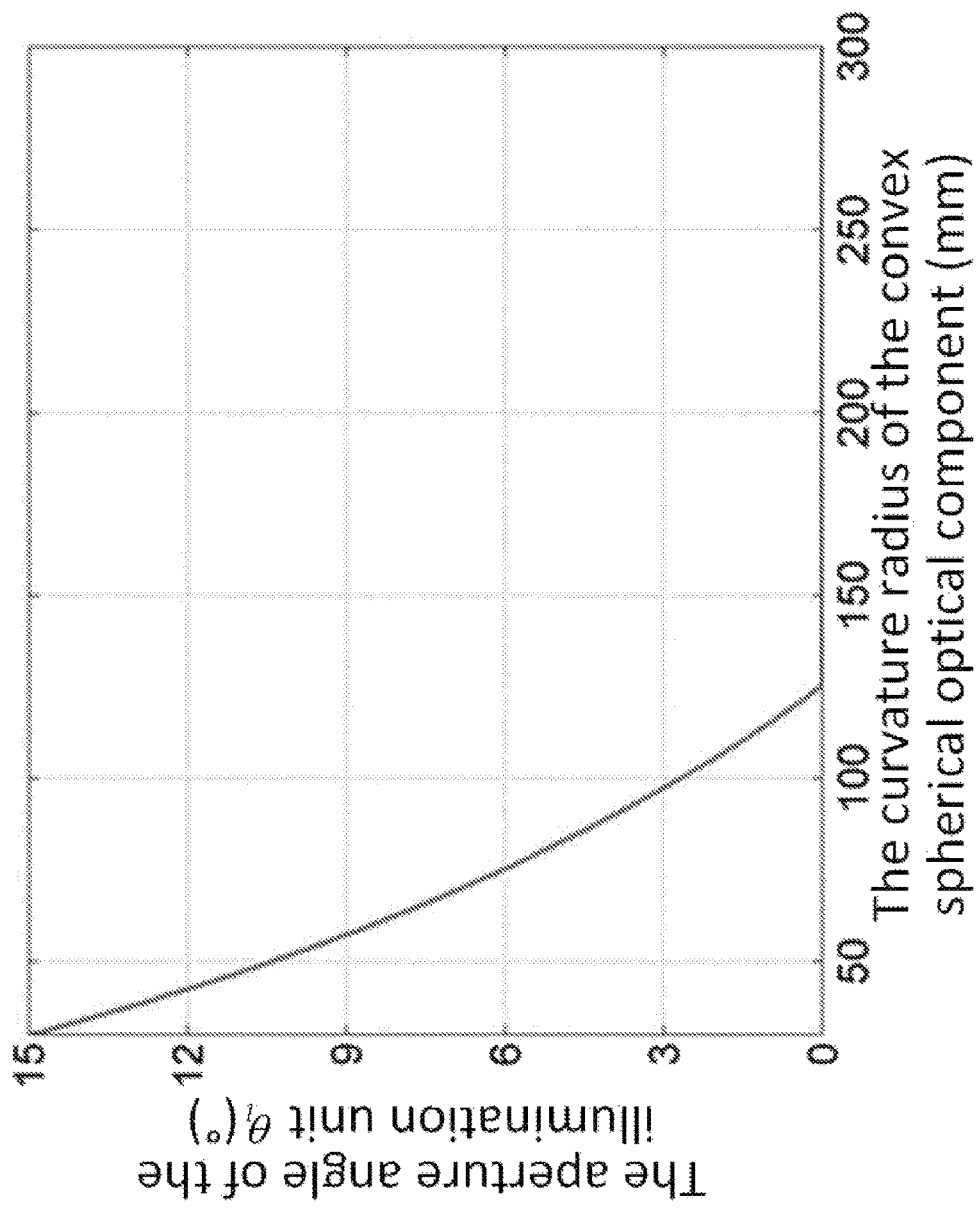
FIG. 5 illustrates a graph of the relationship between the curvature radius of the convex spherical optical component and the aperture angle of the illumination the case of the incident angle of 40° in accordance with FIG. 4.

FIG. 5 illustrates a graph of the relationship between the curvature radius of the convex spherical optical component and the aperture angle $\theta_l$ of the illuminant in the case of the incident angle γ of 40° in accordance with FIG. 4. It can be found that with the curvature radius increasing, the aperture angle $\theta_l$ decreases and the illumination range received by the surface also decreases. The aperture angle $\theta_l$ is less than or equal to 15°.

Taking advantages of the induced scatter light by the principle that defects on the smooth surface modulate the incident light, the MS-DFI unit 400 achieves microscopic dark-field imaging of defects and acquires dark-field images of defects. The MS-DFI unit 400 is the machine vision module of the SSDES 100.

Figure 6:
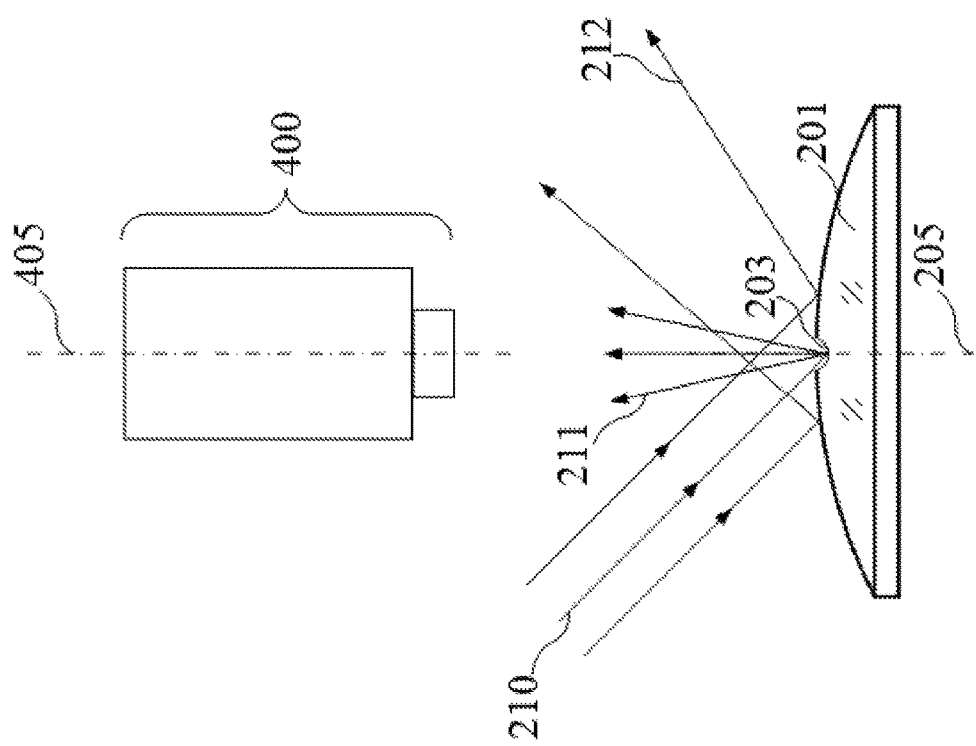
FIG. 6 illustrates a schematic diagram of the principle of the microscopic scattering dark-field imaging of the present invention.

FIG. 6 illustrates a schematic diagram of the principle of the microscopic scattering dark-field imaging of the present invention. The incident light 210 is incident onto the surface of the convex spherical optical component 201. If the spherical surface is smooth, the incident light 210, according to the law of reflection in geometrical optics, is reflected on the surface to form the reflected light 212, which can't enter the MS-DFI unit 400. If there is defect 203 on the surface of the spherical optical component, the incident light 210 is scattered to form the scatter light 211, which is received by the MS-DFI unit 400 and forms the dark-field image of defects.

Figure 2:
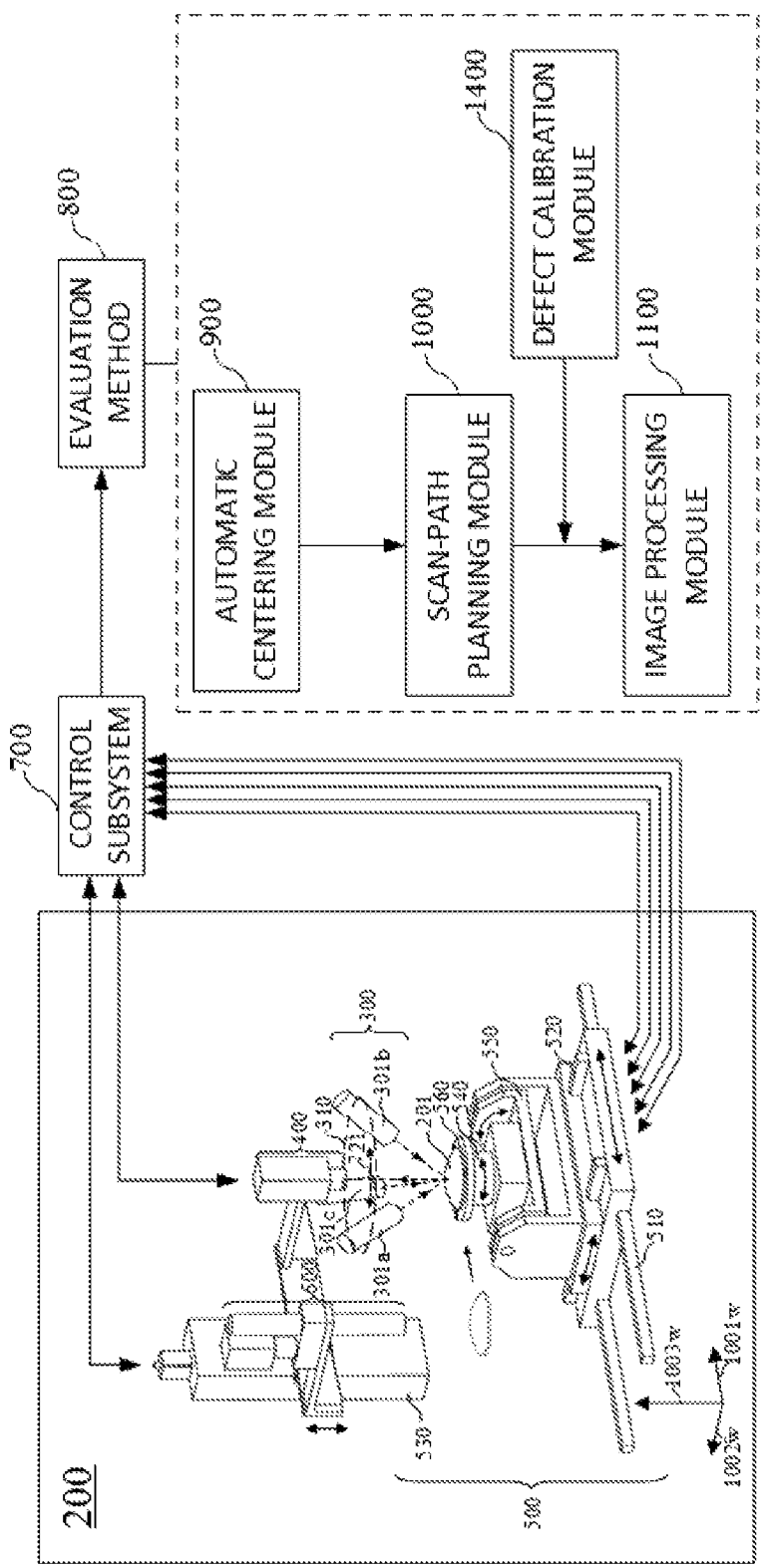
FIG. 2 illustrates a schematic diagram of all parts of surface defects evaluation system and method for spherical optical components in accordance with FIG. 1 in more detail.

The SPPA unit 500 is adapted to achieve adjustment of positions and attitude of the convex spherical optical component 201. FIG. 2 illustrates a schematic diagram of all parts of surface defects evaluation system and method for spherical optical components in accordance with FIG. 1 in more detail. Referring to FIG. 2, the SPPA unit 500 comprises an X-axis translation stage 510, a Y-axis translation stage 520, a Z-axis translation stage 530, a rotation stage 540, a swing stage 550 and a self-centering clamp 560. The swing stage 550 comprises an inner plate and a shell plate. The self-centering clamp 560 has fixed connections with the rotation axis of the rotation stage 540 and the base of the rotation stage 540 is fixed on the inner plate of the swing stage 550. The inner plate has flexible connections with the shell plate so that the inner plate is capable of swinging by the shell plate. The sections of the inner plate and the shell plate are both in U-shape. The undersurface of the shell plate of the swing stage 550 is fixed on the working surface of the Y-axis translation stage 520 and the Y-axis translation stage 520 is fixed on the working surface of the X-axis translation stage 510. The X-axis translation stage 510 and the Z-axis translation stage 530 are fixed on the same platform. The illumination unit 300, the MS-DFI unit 400 and the centering unit 600 are all fixed on the Z-axis translation stage 530.

Figure 7:
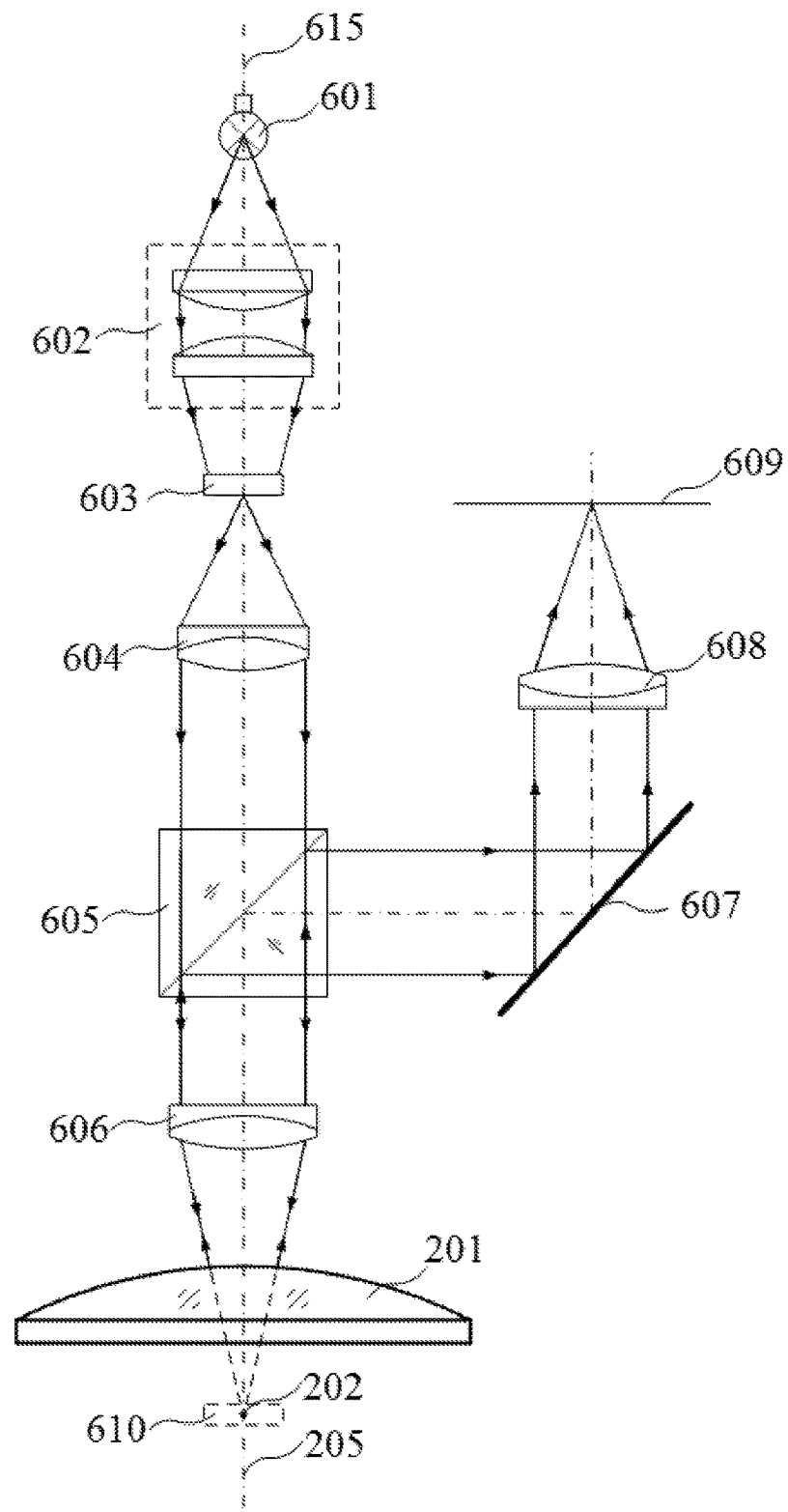
FIG. 7 illustrates a schematic diagram of the structure of the centering unit in accordance with the first embodiment of the present invention.

The centering unit 600 provides hardware basis for the automatic centering of the convex spherical optical component 201. FIG. 7 illustrates a schematic diagram of the structure of the centering unit 600 in accordance with the first embodiment of the present invention. The light beam emitted by the light source 601 of the centering unit 600 passes through the focusing lens group 602 and irradiates the reticle 603 with a crosshair on. Then, the light beam passes through the collimation lens 604, the beam splitter 605 and the objective 606 and irradiates on the convex spherical optical component 201. The light beam is reflected on the surface and the image of the crosshair on the reticle 603 is indicated by the reticle image 610. The reflected light beam passes through the objective 606 again and deflects at the beam splitter 605. Subsequently, the reflected light beam is reflected by the plane reflector 607 and passes through the imaging lens 608. Finally, the light beam focuses on the CCD 609 and the CCD 609 acquires the image of the crosshair on the reticle 603.

Figure 9B:
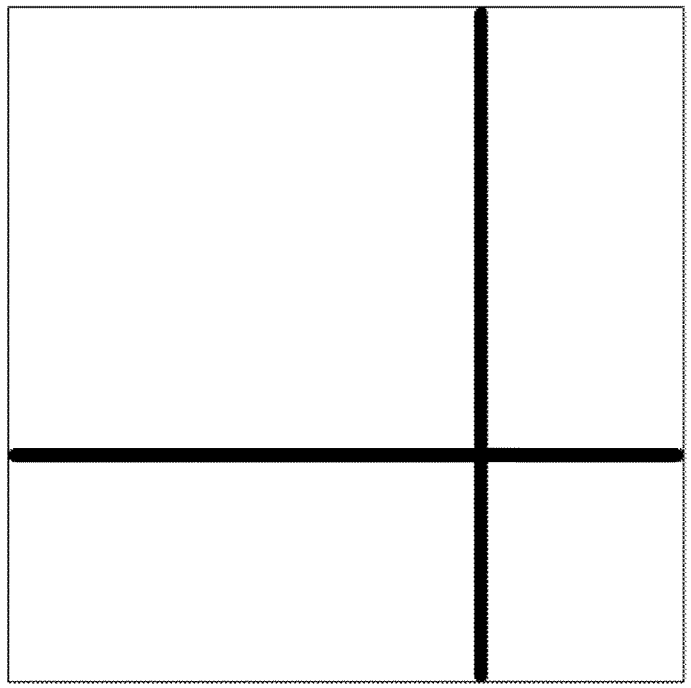
FIG. 9B illustrates an image of the crosshair captured by CCD in the case of X-direction and Y-direction deviation between the positions of the reticle image and the curvature center of the convex spherical optical component in accordance with FIG. 7.
Figure 9A:
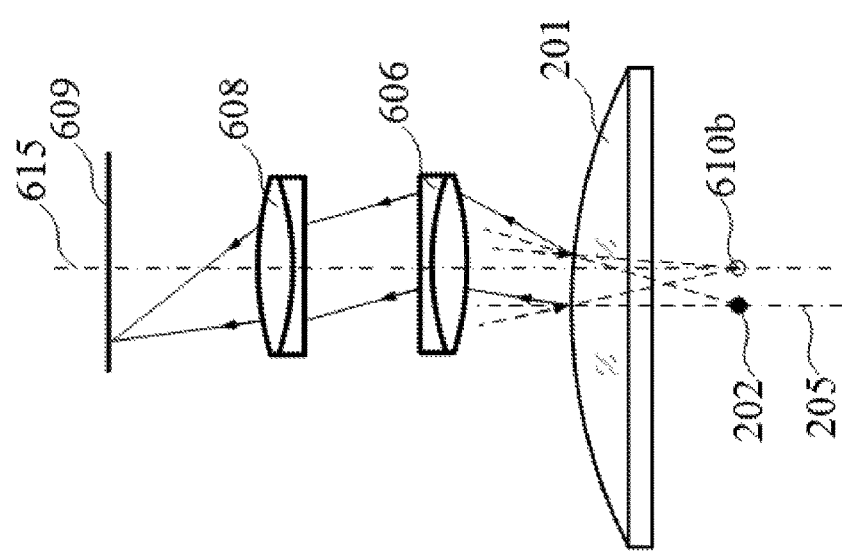
FIG. 9A illustrates a schematic diagram of the light path in the case of X-direction and Y-direction deviation between the positions of the reticle image and the curvature center of the convex spherical optical component in accordance with FIG. 7.

Referring to FIG. 7, if the incident light beam after passing through the objective 606 focuses on the surface of the convex spherical optical component 201, the incident light beam and the reflected light beam are symmetric about the optical axis of the centering unit 615, so the reflected light beam becomes parallel light beam again after passing through the objective 606 the second time and the CCD 609 can acquire sharp crosshair image, which is called the surface image of the crosshair because the image is located on the spherical surface. The position of the surface image in the FOV of the CCD 609 doesn't vary with the slight movement of the convex spherical optical component 201 in X-direction or Y-direction. If the centering unit 600 is moved down to a certain position by the Z-axis translation stage 530, the incident light beam after passing through the objective 606 focuses on the curvature center of the convex spherical optical component 202. In this case, the reticle image 610 is located at the curvature center of the convex spherical optical component 202 and the reflected light beam coincides with the incident light beam. The CCD 609 can also acquire sharp crosshair image, which is called the center image of the cross hair because the image is located at the curvature center of the spherical surface. Therefore, the CCD 609 can acquire sharp crosshair images twice, which are named the surface image and the center image respectively. Thus according to the position and clarity of the crosshair image acquired by CCD 609, the position of the curvature center of the convex spherical optical component 202 can be obtained as follows:

FIG. 8A illustrates a schematic diagram of the light path in the case of Z-direction deviation between the positions of the reticle image 610a and the curvature center of the convex spherical optical component 202 in accordance with FIG. 7. In this case, the reflected light beam doesn't coincide with the incident light beam so that the CCD 609 acquires fuzzy crosshair image, as is illustrated in FIG. 8B. Besides, FIG. 9A illustrates a schematic diagram of the light path in the case of X-direction and Y-direction deviation between the positions of the reticle image 610b and the curvature center of the convex spherical optical component 202 in accordance with FIG. 7. In this case, the optical axis of the convex spherical optical component 205 doesn't coincide with the optical axis of the centering unit 615. The reflected light beam focuses on the CCD 609 so that the CCD 609 acquires sharp crosshair image which is not located in the center of the FOV, as is illustrated in FIG. 9B. Therefore according to the states of crosshair images on the CCD 609, the 3D-position of curvature center of the convex spherical optical component 202 can be determined.

The control subsystem 700 is adapted to drive the movements of various parts of the defect imaging subsystem 200, to realize automatic scanning and inspection of defects on the spherical surface.

Figure 10:
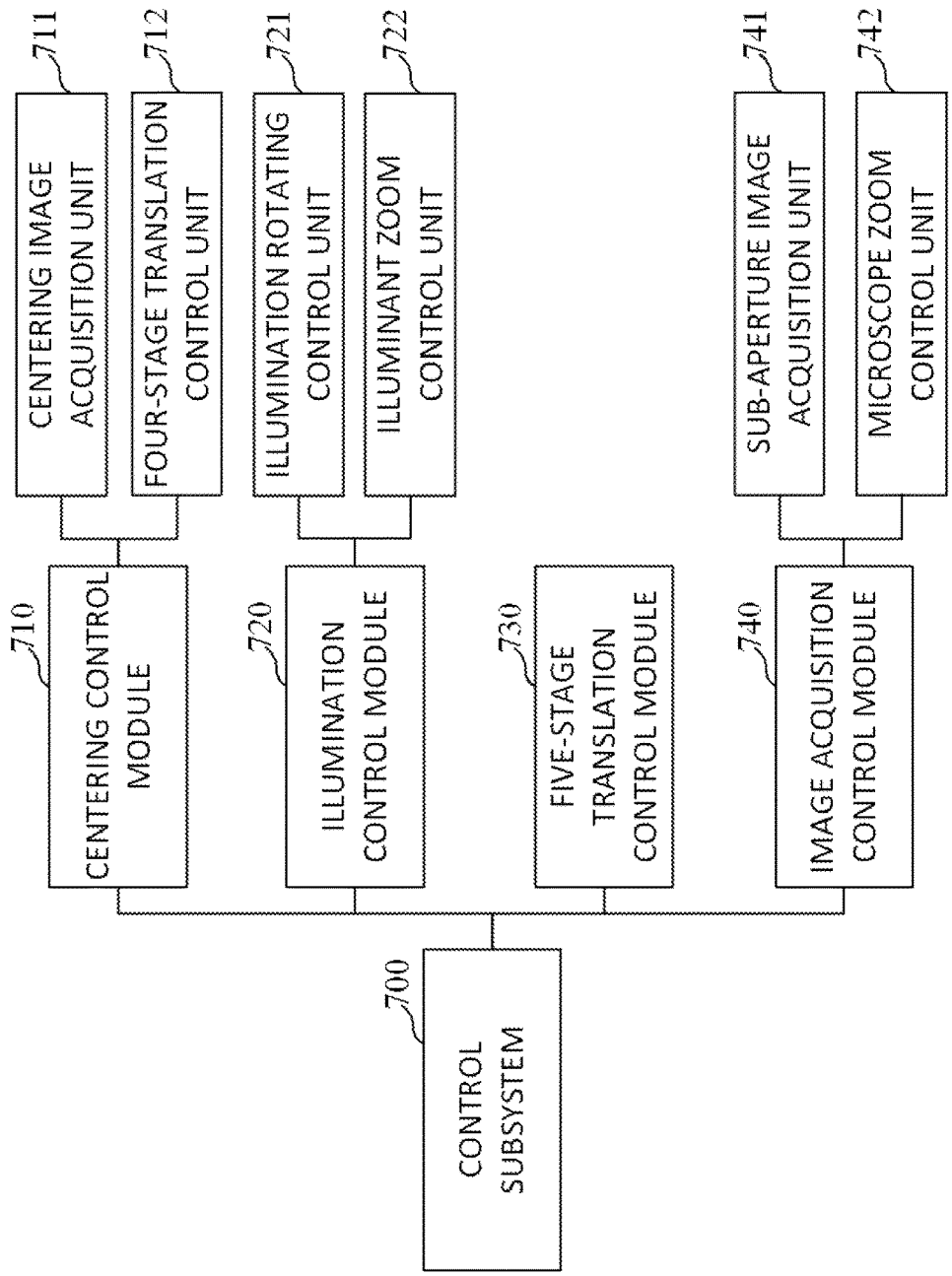
FIG. 10 illustrates a block diagram of the control subsystem in accordance with FIG. 1.

FIG. 10 illustrates a block diagram of the control subsystem 700 in accordance with FIG. 1. The control subsystem 700 comprises a centering control module 710, an illumination control module 720, a five-stage translation control module 730 and an image acquisition control module 740.

Referring to FIG. 10, the centering control module 710 comprises a centering image acquisition unit 711 and a four-stage translation control unit 712. The centering image acquisition unit 711 is applied to control the CCD 609 of the centering unit 600 to acquire the image of the crosshair and the four-stage translation control unit 712 is applied to control the movement of the X-axis translation stage 510, the Y-axis translation stage 520 and the Z-axis translation stage 530 and the rotation of the rotation stage 540 during the process of centering.

Referring to FIG. 10, the illumination control module 720 comprises an illumination rotating control unit 721 and an illuminant zoom control unit 722. The illumination rotating control unit 721 is applied to control the rotation of the illuminant support bracket 310 of the illumination unit 300 and the illuminant zoom control unit 722 is applied to control the movement of the zoom lens group 332 to change the aperture angle $\theta_l$ of the emitted convergent spherical wave.

Referring to FIG. 10, the five-stage translation control module 730 is applied to control the movement of the X-axis translation stage 510, the Y-axis translation stage 520 and the Z-axis translation stage 530, the rotation of the rotation stage 540 and the swing of the swing stage 550 during the process of inspection.

Referring to FIG. 10, the image acquisition control module 740 comprises a sub-aperture image acquisition unit 741 and a microscope zoom control unit 742. The sub-aperture image acquisition unit 741 is applied to control the MS-DFI unit 400 to acquire sub-aperture images and the microscope zoom control unit 742 is applied to change the image magnification of the MS-DFI unit 400.

The SSDES 100 operates in two modes, which are centering mode and inspection mode. FIG. 11A illustrates a schematic diagram of portions of the control subsystem 700 when SSDES 100 operates in centering mode in accordance with FIG. 10. When the convex spherical optical component 201 is located below the centering unit 600 by the SPPA unit 500, the SSDES 100 operates in centering mode. In this mode, the control subsystem 700 achieves automatic centering by the centering image acquisition unit 711 and the four-stage translation control unit 712. The four-stage translation control unit 712 drives the movement of the Z-axis translation stage 530 to make the centering unit 600 focus automatically and accurately along the Z-direction, the movement of the X-axis translation stage 510 and the Y-axis translation stage 520 to realize translation of the convex spherical optical component 201, and rotation of the rotation stage 540.

FIG. 11B illustrates a schematic diagram of portions of the control subsystem 700 when SSDES 100 operates in inspection mode in accordance with FIG. 10. When the convex spherical optical component 201 is located below the MS-DFI unit 400 by the SPPA unit 500, the SSDES 100 operates in inspection mode. In this mode, the control subsystem 700 completes full-aperture defects inspection of the convex spherical optical component 201 by the illumination control module 720, five-stage translation control module 730 and image acquisition control module 740. The illumination control module 720 comprises an illumination rotating control unit 721 and an illuminant zoom control unit 722. The illumination rotating control unit 721 is applied to achieve all-direction illumination for surface defects of the convex spherical optical component 201 and the illuminant zoom control unit 722 is applied to achieve dark-field illumination for surface defects of the convex spherical optical component 201. The five-stage translation control module 730 is applied to drive the convex spherical optical component 201 to precisely adjust the spatial position and posture of the convex spherical optical component 201 for the purpose of full-aperture scanning and inspection. The image acquisition control module 740 comprises a sub-aperture image acquisition unit 741 and a microscope zoom control unit 742. The sub-aperture image acquisition unit 741 is applied to acquire the sub-aperture images for the image processing module 1100 and the microscope zoom control unit 742 is applied to automatically change the imaging magnification of the MS-DFI unit 400.

The control subsystem 700 is the hub of the SSDES 100 connecting the defect imaging subsystem 200 and the evaluation method 800. The control subsystem 700 not only precisely controls the defect imaging subsystem 200, but also delivers images obtained by the defect imaging subsystem 200 and the information of position and state to the evaluation method 800 to process. The control subsystem 700 achieves high-speed delivery and high-efficiency collaborative processing of information between the defect imaging subsystem 200 and the evaluation method 800, realizes automatic scanning of the convex spherical optical component 201 and increases the inspection efficiency of SSDES 100.

The evaluation method 800 comprises an automatic centering module 900, a scan-path planning module 1000, an image processing module 1100 and a defect calibration module 1400.

The automatic centering module 900 is adapted to achieve automatic centering, accurate measurement of the curvature radius and consistency alignment between the rotation axis 565 and the optical axis of the spherical optical component 205. The scan-path planning module 1000 is adapted to plan the optimal scan-path for the spherical surface in order that the whole surface can be inspected without omission by sub-apertures as few as possible. The image processing module 1000 is adapted to achieve spherical surface defects inspection with high precision. The defect calibration module 1400 is adapted to establish the relationship between pixels and actual size in sub-aperture images at any locations on the spherical surface in order that the actual size of defects can be obtained.

The evaluation method 800 comprises the following steps:

Step1: The implementation of automatic centering of the spherical optical component by the automatic centering module 900;

Step2: the completion of optimal scan-path planning and full-aperture scanning for the spherical optical component by the scan-path planning module 1000;

Step3: the obtainment of spherical surface defect information by the image processing module 1100 and the defect calibration module 1400.

Figure 12:
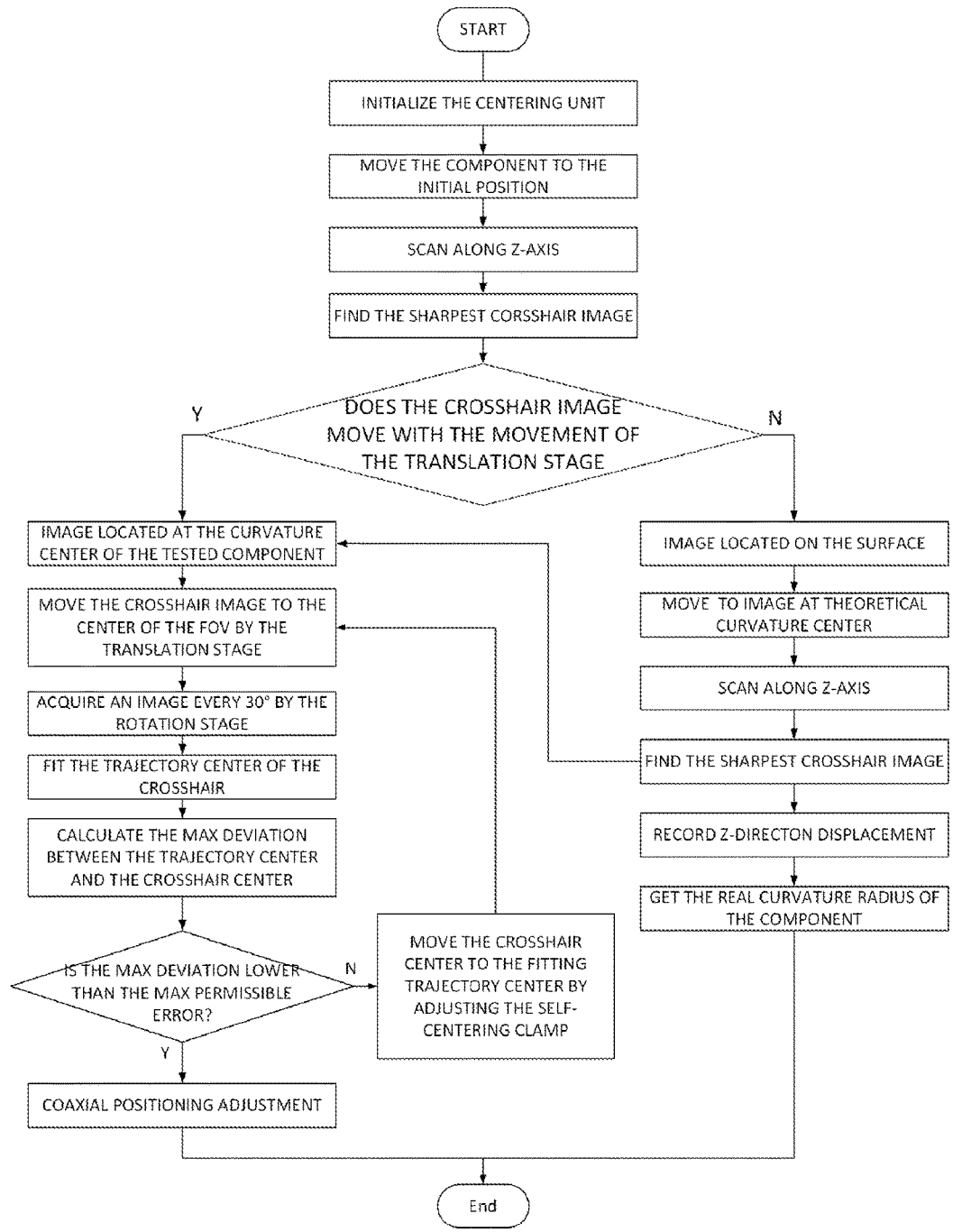
FIG. 12 illustrates a flowchart of the automatic centering module in accordance with FIG. 1.

The implementation of automatic centering of the spherical surface by the automatic centering module 900 according to Step 1, comprises the accurate measurement of the curvature radius of the convex spherical optical component 201 and axial consistency alignment between the rotation axis 565 and the optical axis of the spherical optical component 205, providing fiducial position for planning optimal scan-path in Step 2. FIG. 12 illustrates a flowchart of the automatic centering module 900 in accordance with FIG. 1.

Referring to FIG. 12, the automatic centering module 900 comprises the following steps:

1-1. Initialize the centering unit 600.

1-2. Move the convex spherical optical component 201 to the initial position where the optical axis of the spherical optical component 205 coincides with the optical axis of the centering unit 615 approximately.

Figure 13A:
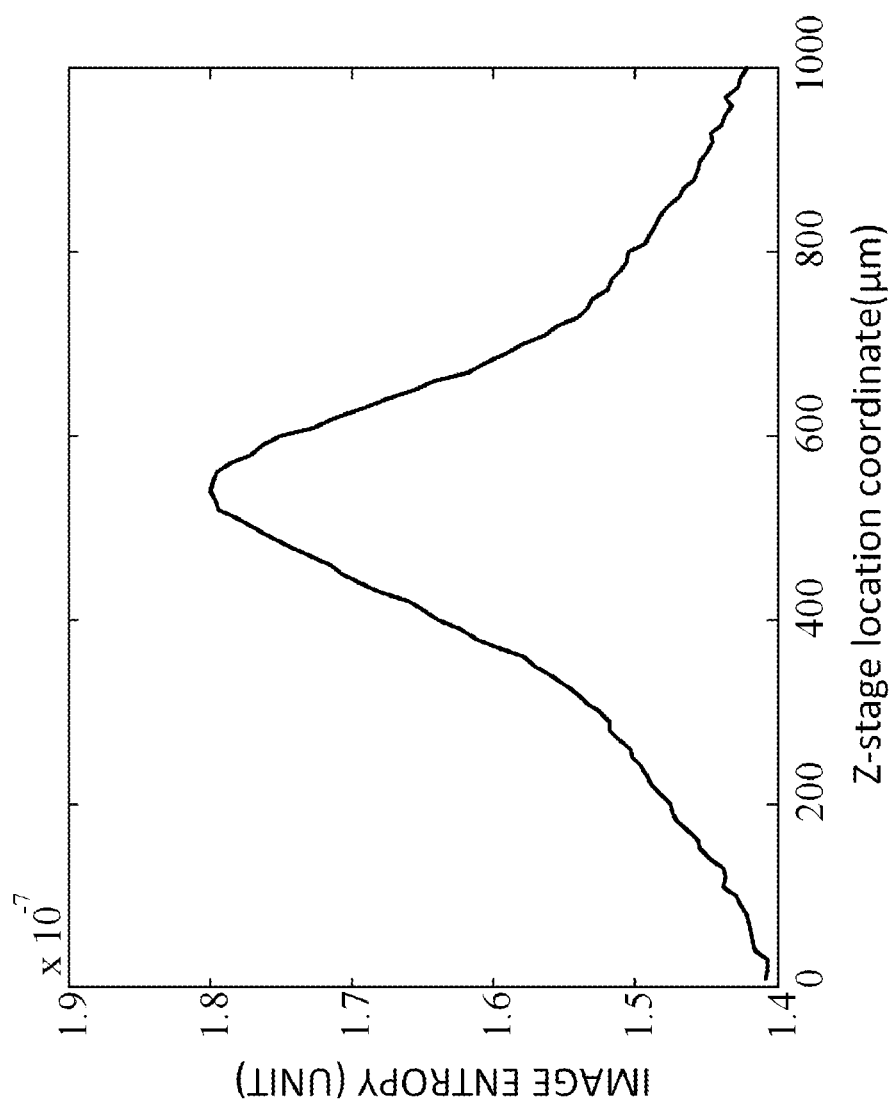
FIG. 13A illustrates a graph of image entropy clarity evaluation function in accordance with FIG. 12.

1-3. The Z-axis translation stage 530 is controlled to scan along Z-direction to find the sharpest crosshair image by use of image entropy clarity evaluation function. FIG. 13A illustrates a graph of image entropy clarity evaluation function in accordance with FIG. 12.

1-4. Judge whether the crosshair image is the surface image or the center image as follows:

Move the X-axis translation stage 510 and Y-axis translation stage 520 slighted to observe whether the crosshair image in the field of view (FOV) is moved with the movement of translation stages or not. If the crosshair image is moved with the movement of stages, it is the center image of the convex spherical optical component 201 and then jump to Step 1-5. Otherwise, it is the surface image of the convex spherical optical component 201 and then jump to Step 1-9.

1-5. Move the crosshair image to the center of FOV by the X-axis translation stage 510 and the Y-axis translation stage 520. After the movement, the optical axis of the convex spherical optical component 205 coincides with the optical axis of the centering unit 615.

Figure 13B:
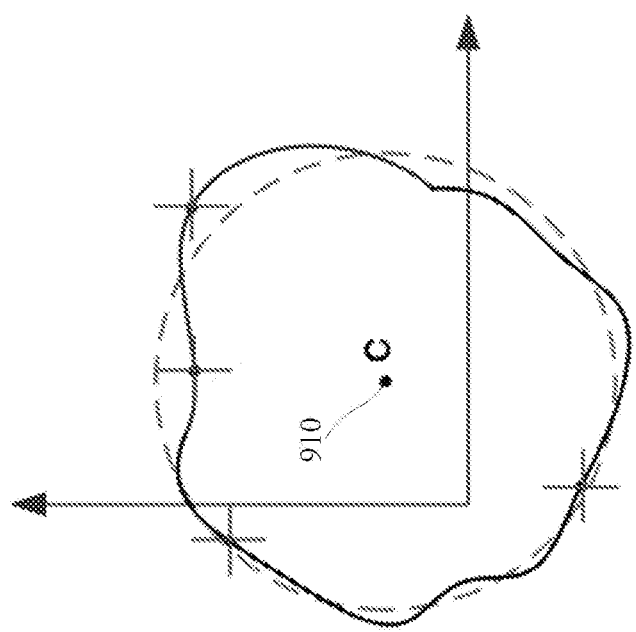
FIG. 13B illustrates a schematic diagram of fitting the trajectory center of the crosshair in accordance with FIG. 12.

1-6. Find the position of the rotation axis 565 by rotation measurement in optical alignment as follows:

The convex spherical optical component 201 can rotate around the rotation axis of the rotation stage 540 under the self-centering clamp 560. Every 30° rotation of the rotation stage 540, CCD 609 acquires a crosshair image. The positions of the crosshair images in the FOV of CCD 609 vary with different rotation angles. The trajectory formed by the center of the crosshair is close to a circle. FIG. 13B illustrates a schematic diagram of fitting the trajectory center of the crosshair in accordance with FIG. 12. Referring to FIG. 13B, the center 910 is the position of the rotation axis 565.

1-7. Obtain the trajectory center by the least square circle fitting method and the max deviation between the trajectory center and the crosshair center is calculated.

1-8. Judge whether the max deviation is lower than the max permissible error. If the max deviation is lower than the max permissible error, the axial consistency alignment is considered completed. Otherwise, the optical axis of the spherical optical component 205 is not coincident with the rotation axis 565, therefore the center of the crosshair image is moved to the fitting trajectory center 910 by adjusting the self-centering clamp 560 and then jump to Step 1-5.

1-9. Move the Z-axis translation stage 530 to image at theoretical curvature center obtained by initialization. The Z-axis translation stage 530 is controlled to scan along Z-direction to find the sharpest crosshair image and then jump to Step 1-5. At the same time, Z-direction displacement from the position of the surface image to the position of the center image is recorded to get the real curvature radius of the convex spherical optical component 201, which is the displacement of the Z-axis translation stage 530.

During the process of centering, the self-centering clamp 560 is adjusted to move the center of the crosshair image to the trajectory center in order that the optical axis of the convex spherical optical component 205 coincides with the rotation axis 565. The X-axis translation stage 510 and the Y-axis translation stage 520 are adjusted to move the crosshair image to the center of the FOV of the CCD 609 in order that the optical axis of the convex spherical optical component 205 coincides with the optical axis of the centering unit 615. After the above adjustment, the optical axis of the convex spherical optical component 205, the rotation axis 565 and the optical axis of the centering unit 615 are in consistency. In this case, the position of the convex spherical optical component 201 is the fiducial position for planning optimal scan-path.

FIG. 14 illustrates a schematic diagram of sub-aperture scanning in accordance with FIG. 1. Referring to FIG. 14A-14F, the completion of optimal scan-path planning and full-aperture scanning for the spherical optical component by the scan-path planning module 1000 according to Step 2, comprises the following steps:

2-1. With the fiducial position obtained in the process of axial consistency alignment in Step 1, the convex spherical optical component 201 is moved by the SSPA unit 500 below the MS-DFI unit 400. Then the MS-DFI unit 400 acquires sub-aperture 1010 located at the vertex of the spherical surface 1009, as is illustrated in FIG. 14A. For the convenience of the following statement, spherical coordinate system $X_sY_sZ_s$ is defined here, whose origin $O_s$ 1004s is located at the curvature center of the convex spherical optical component 201 and the z-axis $Z_s$ 1003s passes through the vertex of the spherical surface 1009. To achieve the full-aperture sampling, two-dimension movements along the meridian and parallel scanning trajectory is required, combining the swing around $X_s$ 1001s and the rotation around $Z_s$ 1003s.

2-2. The convex spherical optical component 201 is driven to swing around $X_s$ 1001s with swing angle $\beta_1$ 1007a, one sub-aperture 1020 is acquired on meridian 1005, as is illustrated in FIG. 14B. After that, rotating around $Z_s$ 1003s with rotation angle $\alpha_1$ 1008a is implemented to acquire another sub-aperture 1020a on parallel 1006a, as is illustrated in FIG. 14C.

2-3. Every time after the rotation around $Z_s$ 1003s with the same rotation angle $\alpha_1$ 1008a, one sub-aperture is acquired so that multiple sub-apertures on parallel 1006a are obtained, as is illustrated in FIG. 14D.

2-4. After the completion of sub-aperture acquisition on parallel 1006a, the convex spherical optical component 201 is driven to swing around $X_s$ 1001s again with swing angle $\beta_2$ 1007b, then one sub-aperture 1030 is acquired on meridian 1005.

2-5. Every time after the rotation around $Z_s$ 1003s with the same rotation angle $\alpha_2$ 1008b, one sub-aperture is acquired so that multiple sub-apertures on parallel 1006b are obtained, as is illustrated in FIG. 14F. Full-aperture sampling is finished with several times repetition of such a process that the convex spherical optical component 201 is driven to swing around $X_s$ 1001s with swing angle $\beta_2$ 1007b to acquire multiple sub-apertures on next parallel after the completion of sub-aperture acquisition on this parallel.

Figure 15:
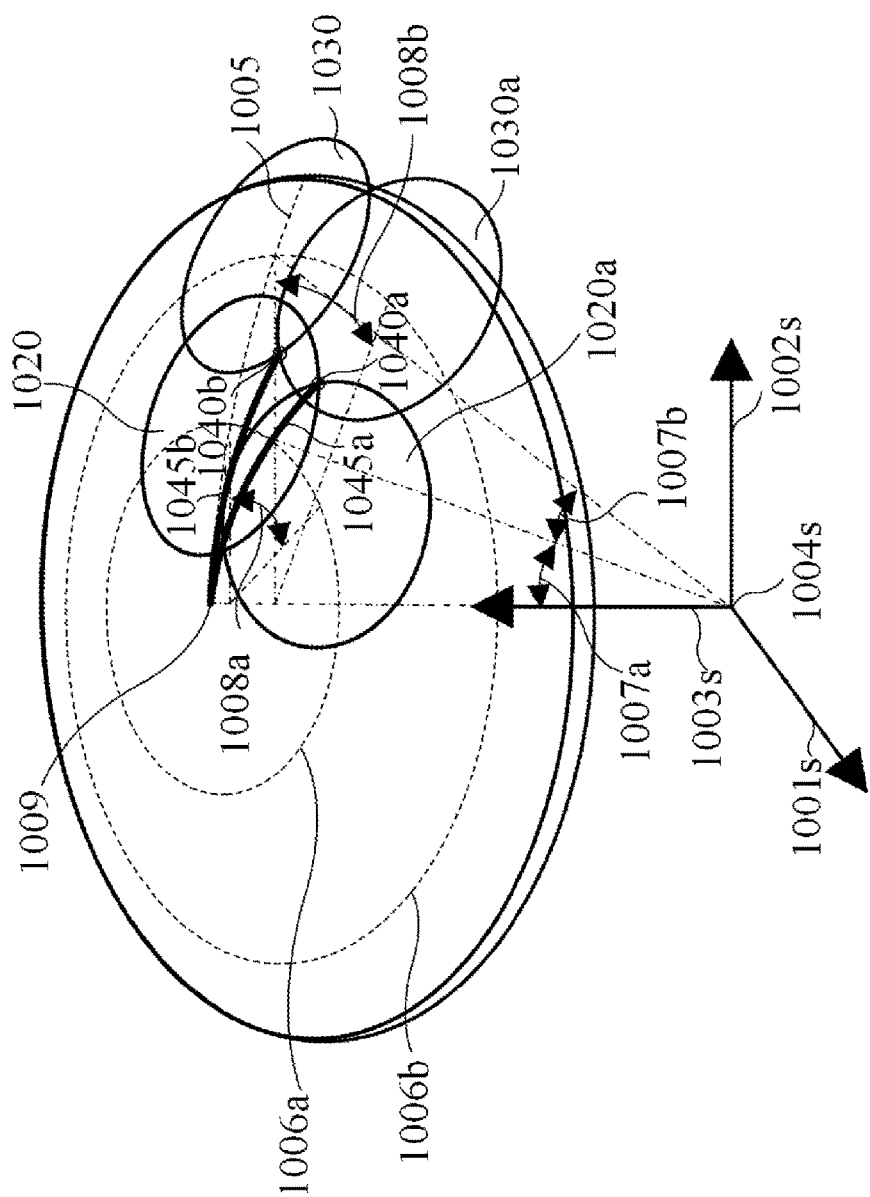
FIG. 15 illustrates a schematic diagram of the sub-aperture plan model in accordance with FIG. 14.
Figure 16:
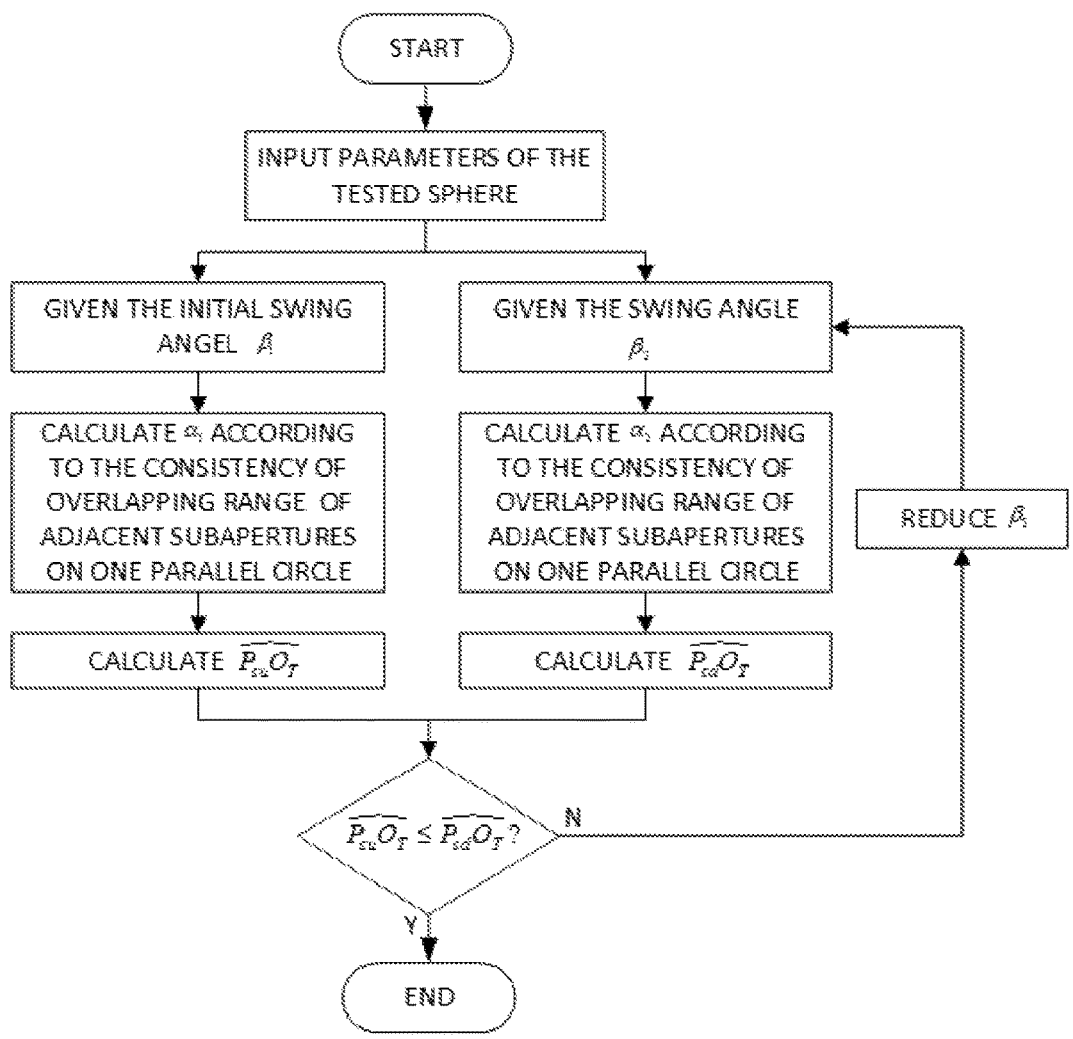
FIG. 16 illustrates a flowchart of the scan-path planning module in accordance with FIG. 14.

FIG. 15 illustrates a schematic diagram of the sub-aperture plan model in accordance with FIG. 14. Referring to FIG. 15, the sub-aperture plan model is established firstly in order that the whole surface can be inspected without omission by sub-apertures as few as possible. In this model, sub-aperture 1020 and sub-aperture 1030 are two adjacent sub-apertures on meridian 1005. Sub-aperture 1020a is adjacent to sub-aperture 1020 on parallel 1006a where sub-aperture 1020 is located. Similarly, sub-aperture 1030a is adjacent to sub-aperture 1030 on parallel 1006b where sub-aperture 1030 is located. Besides, the bottom intersection of sub-aperture 1020 and sub-aperture 1020a (the intersection far from the vertex of the spherical surface 1009) is indicated by $P_{cd}$ 1040a, the top intersection of sub-aperture 1030 and sub-aperture 1030a (the intersection near the vertex of the spherical surface 1009) is indicated by $P_{cu}$ 1040b. So the sufficient conditions for the realization of sub-aperture no-leak inspection is that the arc length $\overparen{P_{cu}O_i}$ 1045b is less than or equal to the arc length $\overparen{P_{cd}O_i}$ 1045a. Under such a constraint, planning result can be solved and obtained by establishing the relationship between swing angle $\beta_1$ 1007a, swing angle $\beta_2$ 1007b and rotation angle $\alpha_1$ 1008a, rotation angle $\alpha_2$ 1008b. The solution procedure of swing angle $\beta_1$ 1007a, swing angle $\beta_2$ 1007b, rotation angle $\alpha_1$ 1008a and rotation angle $\alpha_2$ 1008b is as follows:

① Validate relevant parameters about the convex spherical optical component 201, including the curvature radius, aperture of the convex spherical optical component 201 and the size of the object field of view of the MS-DFI unit 400.

② Specify the initial value of swing angle $\beta_1$ 1007a and swing angle $\beta_2$ 1007b according to the above three parameters. After that, calculate the value of rotation angle $\alpha_1$ 1008a and rotation angle $\alpha_2$ 1008b according to the same overlapping area between adjacent sub-apertures on one parallel. Then, figure out arc length $\overparen{P_{cu}O_i}$ 1045b and arc length $\overparen{P_{cd}O_i}$ 1045a.

③ Compare arc length $\overparen{P_{cu}O_i}$ 1045b and arc length $\overparen{P_{cd}O_i}$ 1045a to determine whether the given initial value of swing angle $\beta_2$ 1007b is appropriate or not. If $\overparen{P_{cu}O_i} > \overparen{P_{cd}O_i}$, reduce the value of swing angle $\beta_2$ 1007b by 5% and then jump to Step ②. Otherwise, sub-aperture plan for covering the entire spherical surface is finished.

Figure 17:
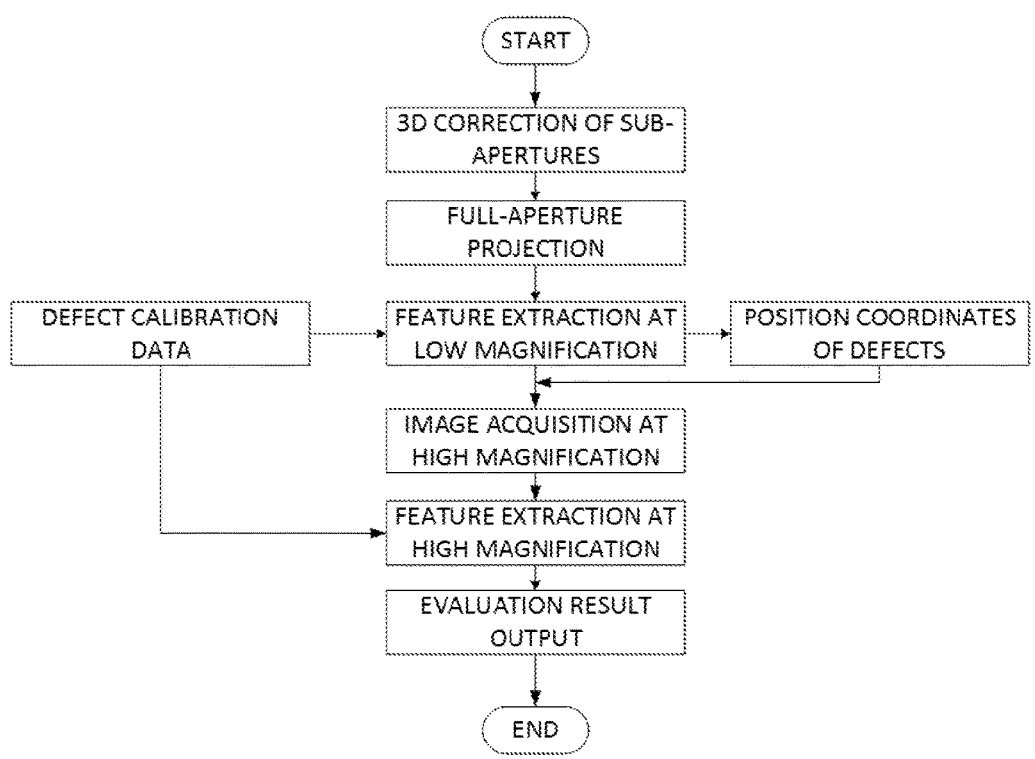
FIG. 17 illustrates a flowchart of the image processing module in accordance with FIG. 1.

FIG. 17 illustrates a flowchart of the image processing module 1100 in accordance with FIG. 1. Referring to FIG. 17, the obtainment of spherical surface defects information by the image processing module 1100 and the defect calibration module 1400 according to Step 3, comprises the following steps:

3-1. The imaging sub-aperture image is a 2D image, which is obtained when the surface of the convex spherical optical component 201 is imaged by the MS-DFI unit 400 in the image plane. Due to the information loss along the direction of optical axis during the optical imaging process, 3D correction of sub-apertures should be conducted firstly to recover the information loss of surface defects of the convex spherical optical component 201 along the direction of optical axis during the optical imaging process.

3-2. For convenience of feature extraction, 3D sub-aperture images obtained after 3D correction of sub-apertures are projected onto a 2D plane with the full-aperture projection to obtain the full-aperture projective image.

3-3. Feature extraction at low magnification is conducted on the full-aperture projective image; then 3D sizes of defects is obtained with inverse-projection reconstruction; finally, actual sizes and positions of surface defects on the convex spherical optical component 201 are obtained taking advantages of the defect calibration data got with the calibration module 1400.

3-4. Defects are inspected at high magnification to guarantee the micron-scale inspection precision. First, the imaging magnification of the MS-DFI unit 400 is zoomed to high magnification; then, according to the positions obtained by Step 3-3, surface defects are moved to the center of the object field of view to acquire images at high magnification; Finally, feature extraction at high magnification is conducted and micron-scale evaluation results of defects are obtained taking advantages of the defect calibration data got with the calibration module 1400.

3-5. Evaluation results are output in the form of 3D panoramic preview of the spherical surface, electronic report and defect location map.

Figure 18:
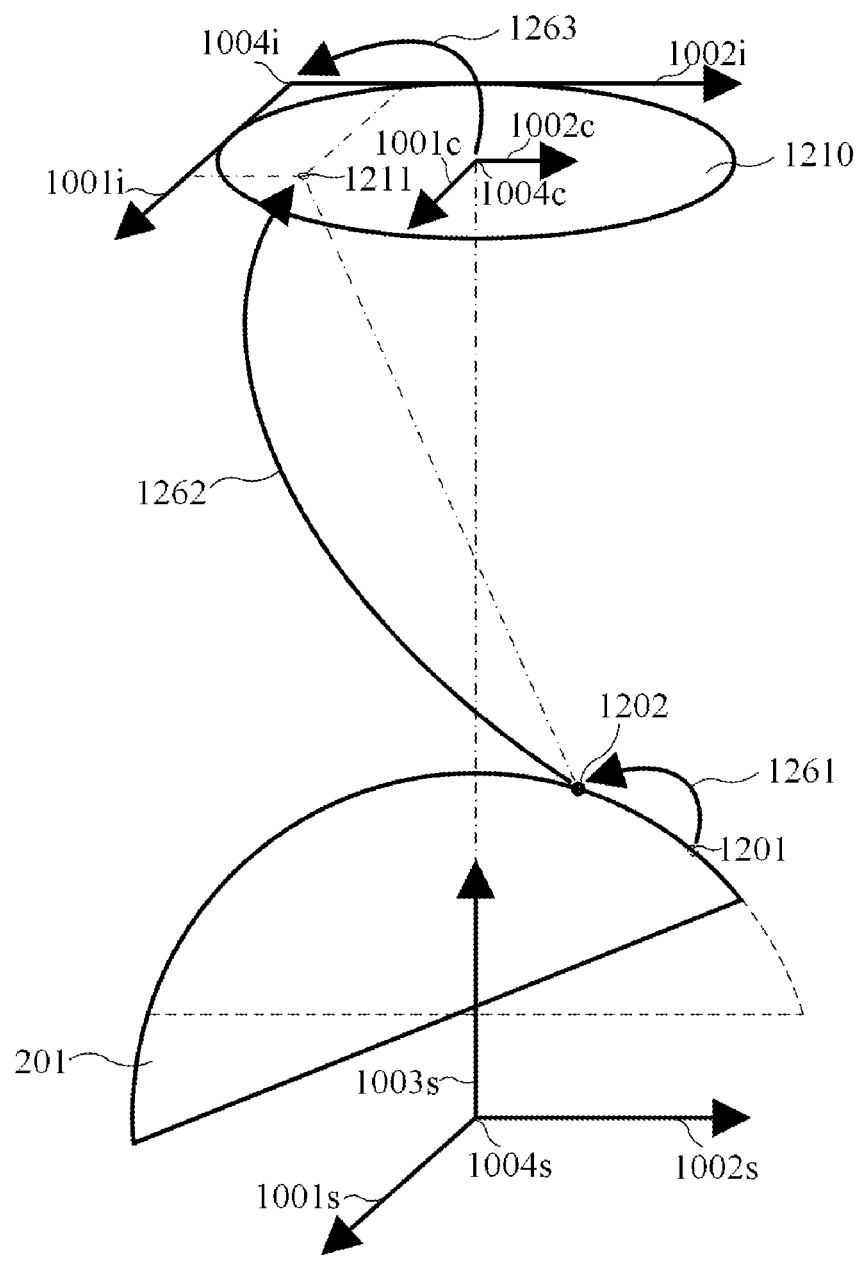
FIG. 18 illustrates a schematic diagram of the imaging process of the sub-aperture in accordance with FIG. 17.

FIG. 18 illustrates a schematic diagram of the imaging process of the sub-aperture in accordance with FIG. 17. According to Step 3-1, imaging sub-aperture images are obtained when the surface of the convex spherical optical component 201 is imaged by MS-DFI unit 400 in the image plane. Referring to FIG. 17, the detailed description is as follows:

3-1-1. According to the optimal scan-path planned by the scan-path planning module 1000 in Step 2, one point p 1201 on the surface of the convex spherical optical component 201 is moved to the point p' 1202 by the SPPA unit 500, as is illustrated by Procedure 1261 in FIG. 18.

3-1-2. The MS-DFI unit 400 acquires sub-apertures at low magnification. Point p' 1202 is imaged to be image point p" 1211 in the imaging sub-aperture image 1210 by the MS-DFI unit 400, as is illustrated by Procedure 1263 in FIG. 18.

3-1-3. During the process of digital image acquisition, the image-plane coordinate system $X_cY_c$ is transformed into the image coordinate system $X_iY_i$ and imaging sub-aperture image 1210 obtained, as is illustrated by Procedure 1263 in FIG. 18. Referring to FIG. 18, X-axis $X_c$ 1001c and y-axis $Y_c$ 1002c compose the image-plane coordinate system $X_cY_c$, whose origin $O_c$ 1004c is located at the intersection of the optical axis of the MS-DFI unit 405 and the imaging sub-aperture image 1210. X-axis $X_i$ 1001i and y-axis $Y_i$ 1002i compose the image coordinate system $X_iY_i$, whose origin $O_i$ 1004i is located at the top left corner of the digital image.

Figure 19:
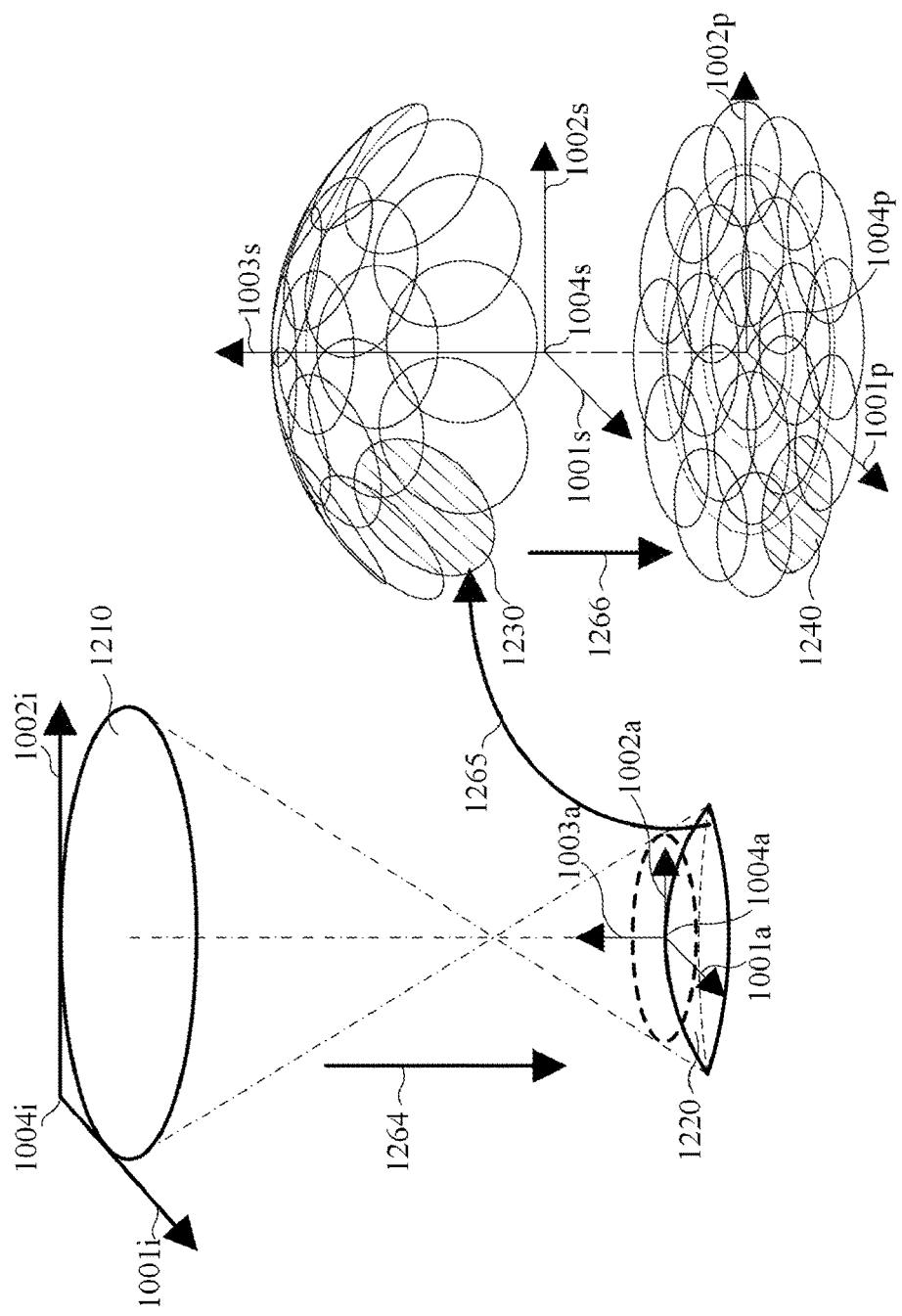
FIG. 19 illustrates a schematic diagram of the 3D correction of the sub-aperture, image stitching of spherical sub-aperture images and full-aperture projection in accordance with FIG. 17.
Figure 20:
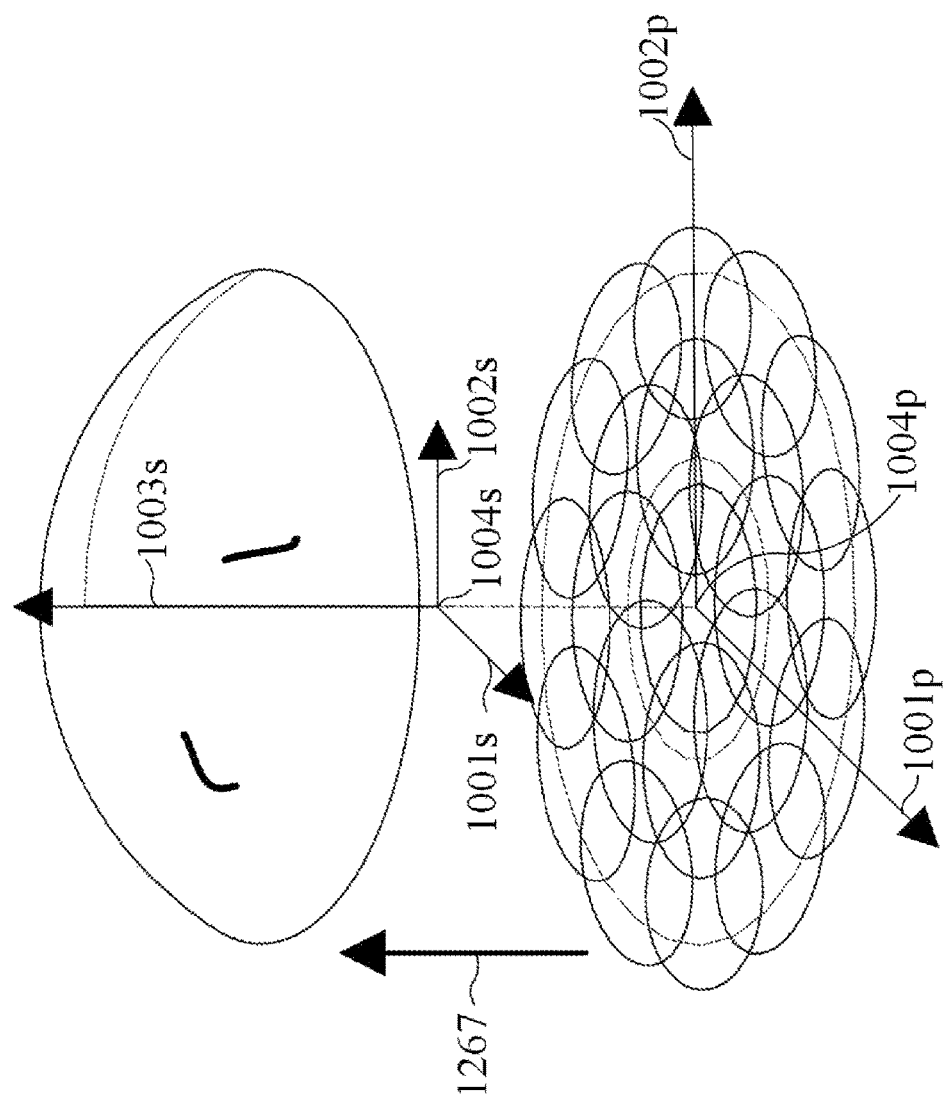
FIG. 20 illustrates a schematic diagram of inverse-projection reconstruction of projective sub-aperture images in accordance with FIG. 17.

As is illustrated by Procedure 1264 in FIG. 19, 3D correction of sub-apertures according to Step 3-1 means that the imaging process of MS-DFI unit 400 is simplified to be a pin-hole model and imaging sub-aperture image 1210 are transformed into 3D sub-aperture image 1220 with geometrical relationship.

Figure 21:
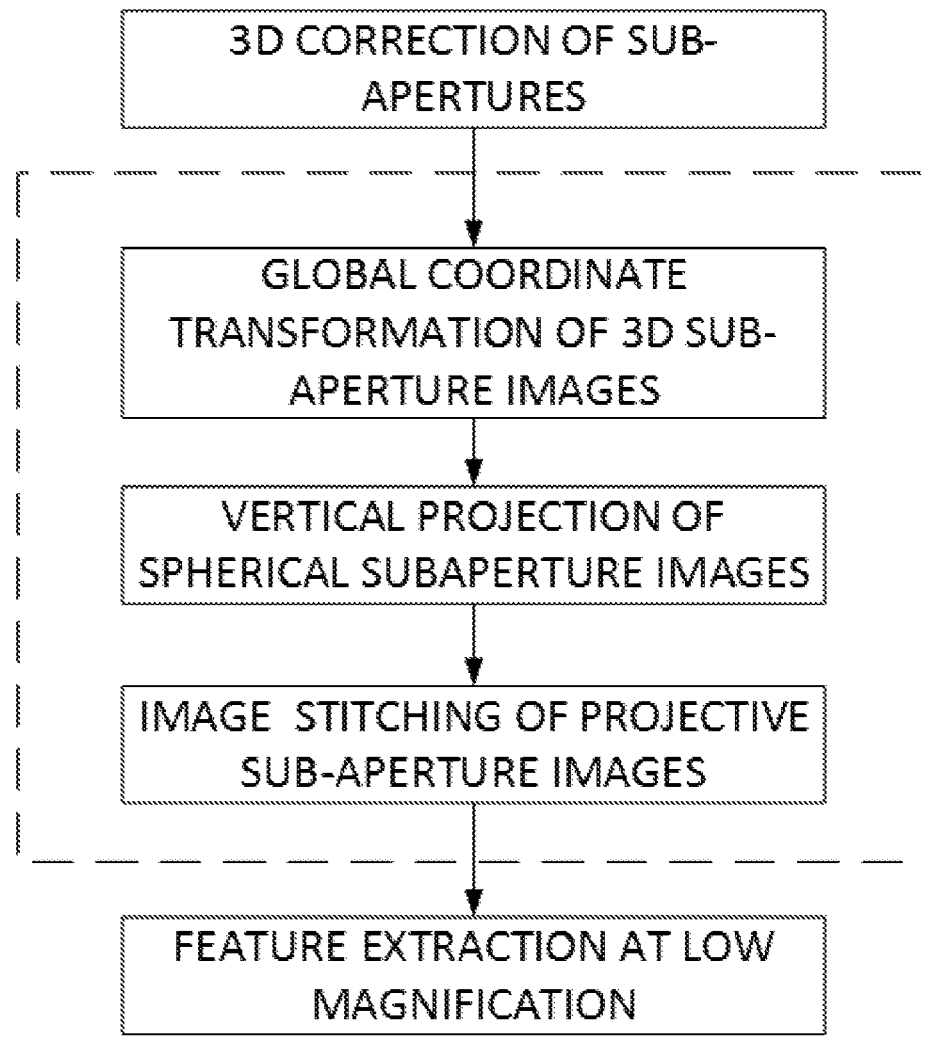
FIG. 21 illustrates a flowchart of full-aperture projection in accordance with FIG. 17.

FIG. 19 illustrates a schematic diagram of the 3D correction of the sub-aperture, image stitching of spherical sub-aperture images and full-aperture projection in accordance with FIG. 17. FIG. 21 illustrates a flowchart of full-aperture projection in accordance with FIG. 17. According to Step 3-2, the full-aperture projective image is obtained. Referring to FIGS. 19 and 21, the detailed description is as follows:

3-2-1. 3D sub-aperture image 1220 is transformed into spherical sub-aperture image 1230 by global coordinate transformation, as is illustrated by Procedure 1265 in FIG. 19.

3-2-2. Spherical sub-aperture image 1230 is projected vertically onto the plane to obtain projective sub-aperture image 1240, as is illustrated by Procedure 1266 in FIG. 19. In this way, data volume describing one sub-aperture is reduced so that computations of the following feature extraction can be largely simplified.

3-2-3. In terms of inspection for surface defects of the convex spherical optical component 201 involving multiple sub-apertures, perfect stitching should be carried out before extracting sizes and positions of defects. Since it is difficult to extract sizes and positions of defects in three-dimensional space, spherical sub-aperture image 1230 is projected vertically onto the plane to obtain projective sub-aperture image

1240. Projective sub-aperture images are stitched and sizes and positions of defects are extracted in the plane. Precise inspection for surface defects of the convex spherical optical component 201 can be achieved by inverse-projection reconstruction.

Figure 22:
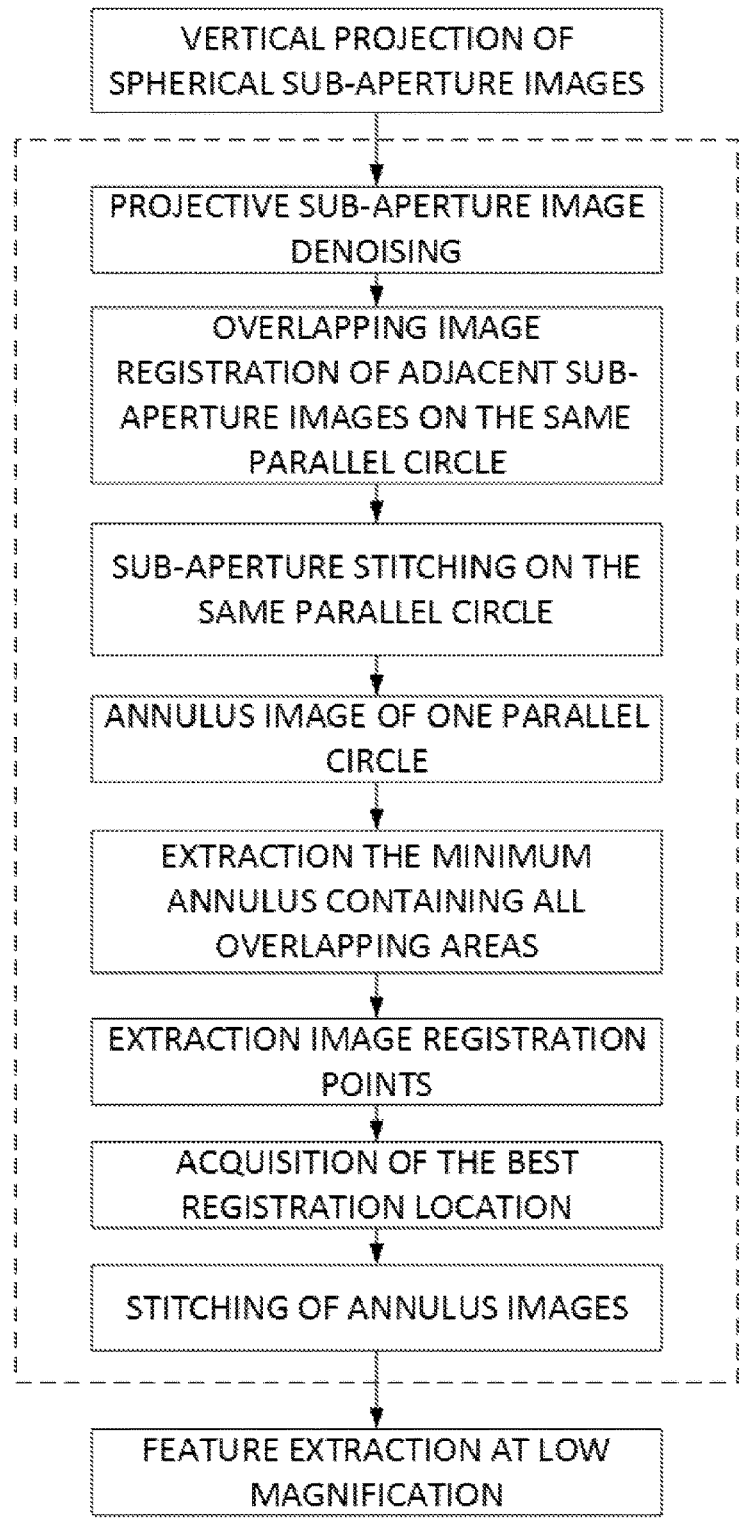
FIG. 22 illustrates a flowchart of image stitching of projective sub-apertures in accordance with FIG. 21.

The way of direct stitching for parallel circle and annulus stitching for meridian circle is used for image stitching of projective sub-aperture images. FIG. 22 illustrates a flowchart of image stitching of projective sub-apertures in accordance with FIG. 21. Referring to FIG. 22, the process of image stitching of projective sub-aperture images is as follows:

① Projective sub-aperture images are denoised to remove the effect of background noise on stitching accuracy.

② After denoising, image registration according to overlapping area is carried out on adjacent projective sub-aperture images on the same parallel circle.

③ Adjacent projective sub-aperture images after registration on the same parallel circle are stitched to obtain the annulus image of one parallel circle.

④ The minimum annulus image containing all overlapping areas is extracted.

⑤ The image registration points of the minimum annulus image are extracted to acquire the best registration location, so that the image stitching of projective sub-aperture images is finished.

Referring to FIG. 19, during the process of vertical projection, spherical sub-aperture image 1230 after global coordinate transformation has difference in deformation and compression of defects. Thus, during the following process of feature extraction at low magnification, inverse-projection reconstruction is needed to recover the deformation and compression due to the vertical projection of spherical sub-aperture image 1230.

According to Step 3-3, feature extraction at low magnification is conducted on the full-aperture projective image; then, 3D sizes of defects is obtained with inverse-projection reconstruction; finally, actual sizes and positions of surface defects of the spherical optical component are obtained taking advantages of the defect calibration data got with defect calibration module 1400. The detailed description is as follows.

3-3-1. Extract features of the 2D full-aperture image after image stitching of projective sub-aperture images to obtain sizes and positions of defects.

3-3-2. Obtain 3D sizes and positions in pixels of surface defects of the convex spherical optical component 201 by inverse-projection reconstruction, as is illustrated by Procedure 1267 in FIG. 20.

3-3-3. Taking advantages of the defect calibration data got with the defect calibration module 1400, convert 3D sizes and positions in pixels to actual sizes and positions.

The defect calibration data according to Step 3-3 and Step 3-4 comprises defect length calibration data and defect width calibration data. The sizes and position coordinates of defects are quantified in pixels after image processing module 1100, thus the defect calibration module 1400 is needed to establish the relationship between actual sizes of line segments at any locations on the spherical surface and corresponding pixels in sub-aperture images for purpose of actual lengths, widths and position coordinates of defects.

Figure 23:
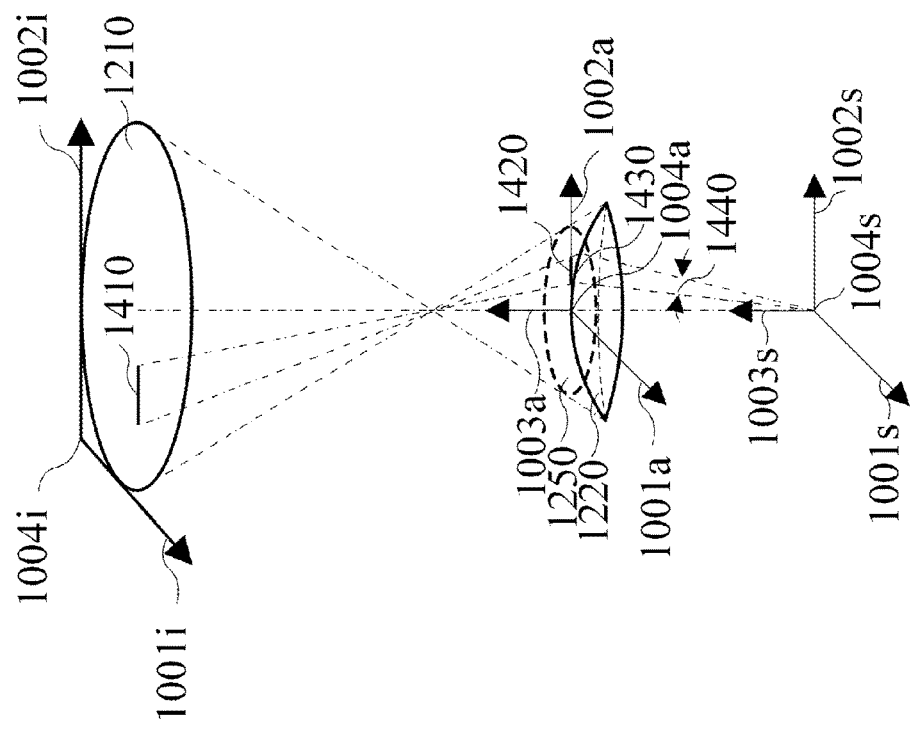
FIG. 23 illustrates a schematic diagram of the process of defect length calibration.

The process of defect length calibration is to establish the relationship between actual lengths of line segments at any locations on the spherical surface and corresponding pixels in spherical sub-aperture images. FIG. 23 illustrates a schematic diagram of the process of defect length calibration. Referring to FIG. 23, The defect length calibration data is obtained as follows:

Firstly, a standard line segment $d_l$ 1420 is taken in the object plane 1250 and its length is measured by a standard measuring instrument. Standard line segment $d_l$ 1420 is imaged by MS-DFI unit 400 and its image $d_p$ 1410 can be obtained in the imaging sub-aperture image 1210.

Then, this imaging sub-aperture image 1210 is transformed into a 3D sub-aperture image 1220 by 3D correction, in which the spherical image of standard line segment $d_l$ 1420, namely a short arc $d_c$ 1430 on the spherical surface can be obtained. The size of $d_c$ 1430 is quantified in pixels and its corresponding arc angle $d_\theta$ 1440 is obtained. Since the curvature radius R of the convex spherical optical component 201 can be determined accurately during the process of centering, the corresponding actual size of $d_c$ 1430 can be deduced by $d=Rd_\theta$. By establishing the relationship between $d_c$ and $d$, the relationship between the pixels in the 3D sub-aperture image 1220 and the actual size is calibrated, namely the calibration coefficient $k=d/d_c$. If substituting the equation $d=Rd_\theta$, we have $k=Rd_\theta/d_c$. Continuing to substitute the equation $d_c=R_{pixel}d_\theta$, we can finally deduce calibration coefficient by $k=R/R_{pixel}$, where $R_{pixel}$ is the curvature radius in pixels of the 3D spherical surface image, called pixel curvature radius for short. Thus it can be seen that the calibration coefficient k varies with the curvature radius R and calibration should be carried out again if the curvature radius R changes.

To extract the length of surface defects on one spherical optical component, feature extraction is firstly implemented to get each pixel's position coordinates of defects. Then the continuous defects are discretized into a plurality of line segments described by a series of line equations $l_i$: $y_i=k_ix_i+b_i$ based on position coordinates, where i=1, 2, 3 . . . n. After the process of inverse-projection reconstruction for each line segment, the corresponding arc $C_i$ of line segment $l_i$ on the spherical surface with the curvature radius $R_{pixel}$ is obtained. And the length of defects in pixels can be figured out with the surface integral equation:

$$L_{pixel} = \sum_{i=1}^{n} \left( \int_{C_i} ds \right)$$

where ds refers to the curve differential element. After substituting the calibration coefficient k, the actual length of defects can be obtained by:

$$L_{real} = \sum_{i=1}^{n} k_i \left( \int_{C_i} ds \right)$$

Figure 24:
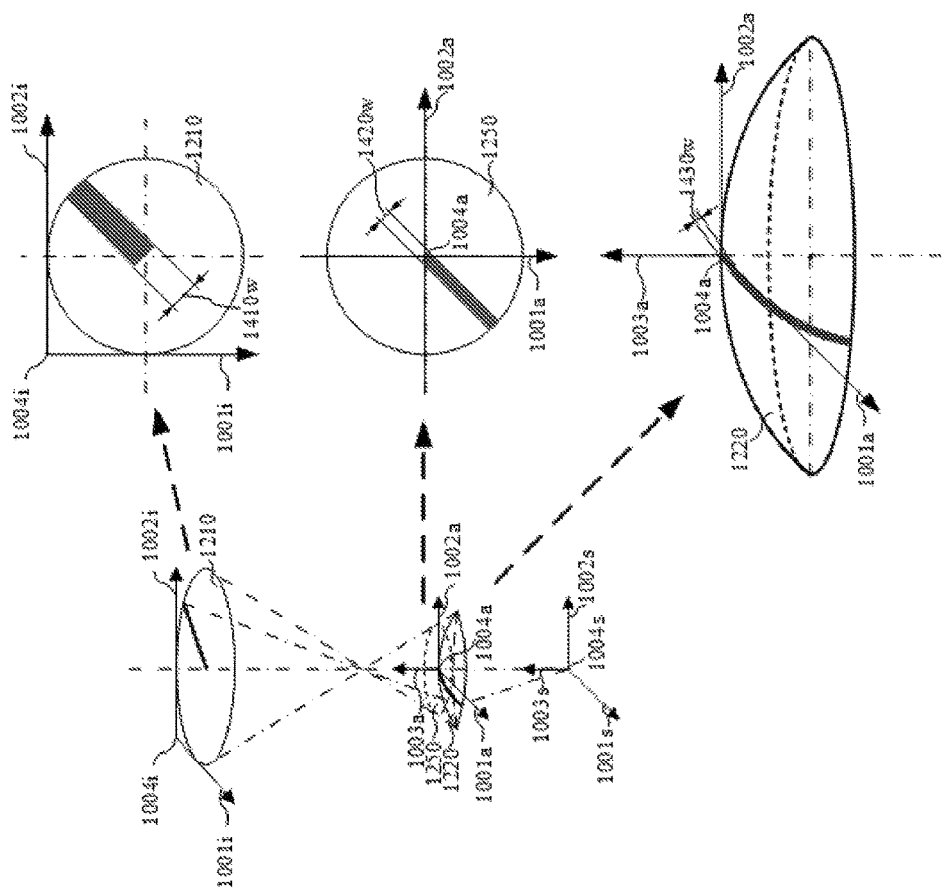
FIG. 24 illustrates a schematic diagram of the process of defect width calibration.

The purpose of width calibration is to establish the relationship between actual length of standard line segments at any locations on the spherical surface and corresponding pixels in 3D sub-aperture images. When MS-DFI unit 400 works at low magnification, the width in micron-scale is difficult to be calibrated accurately due to its small FOV and low resolution. So the width calibration results obtained at low magnification could not be used for evaluation, but only for reference. Defects width should be calibrated and evaluated at high magnification. At low magnification, the method similar to that for the process of length calibration is applied to the process of width calibration. FIG. 24 illustrates a schematic diagram of the process of defect width calibration. At high magnification, referring to FIG. 24, since defects width is in micron-scale and defects are located in the center of the FOV, the defect width calibration data is obtained as follows:

Firstly, in the 3D coordinate system, a standard line segment is taken in the object plane 1250 and its actual width 1420w is measured by a standard measuring instruments. The standard line segment is imaged by the MS-DFI unit 400 and its image can be obtained in the imaging sub-aperture image 1210 with imaging width 1410w in pixels.

Then, this imaging sub-aperture image 1210 is transformed into 3D sub-aperture image 1220 by 3D correction, in which the spherical image of the standard line segment can be obtained. For the spherical image, the arc length 1430w in pixels along width direction is the width of defects in pixels.

Since the defects are located in the center of FOV during the process of image acquisition at high magnification, information loss along the direction of the optical axis can be ignored. Thus, the actual width of defects is equal to the width of the standard line segment 1420w.

Figure 25:
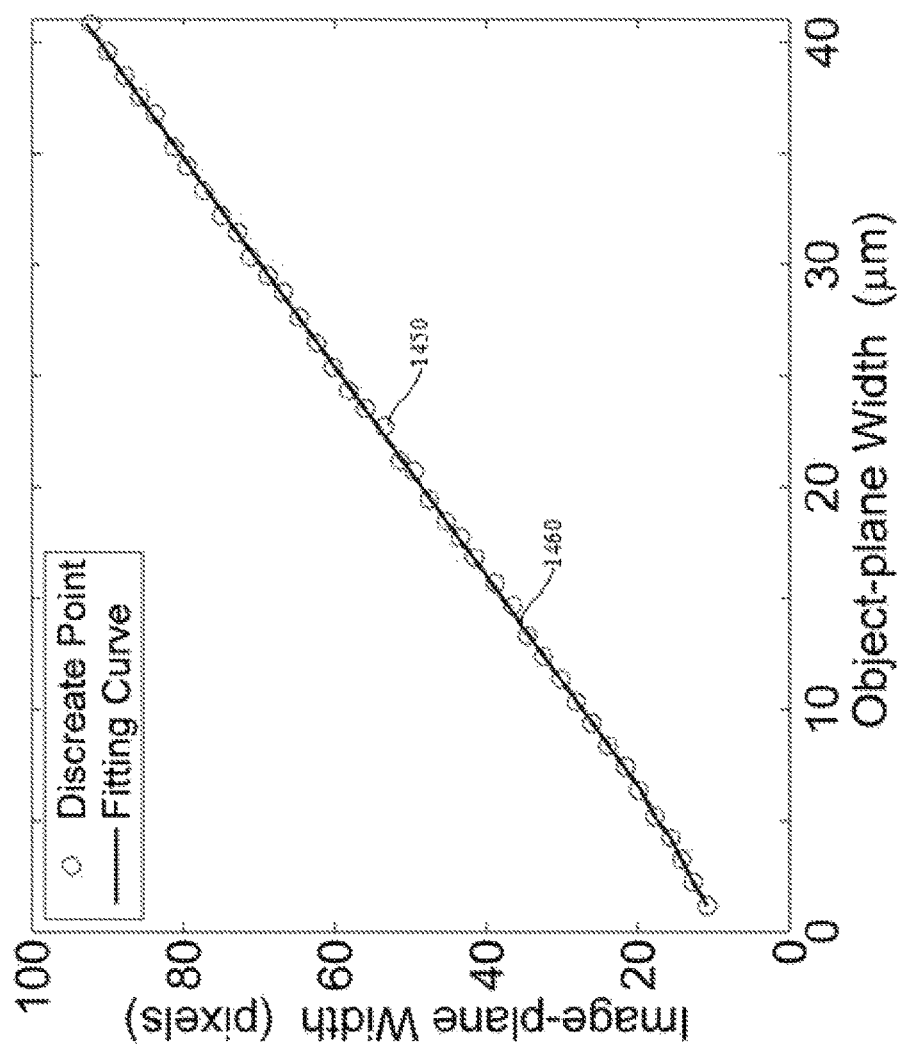
FIG. 25 illustrates a graph of the calibration transfer function for width in accordance FIG. 24.

FIG. 25 illustrates a graph of the calibration transfer function for width in accordance FIG. 24.

Finally, a piecewise fitting for the corresponding discrete points 1450 of actual width and width in pixels of defects is used to obtain the best fitting curve, which is as the calibration transfer function (CTF) 1460. With the CTF 1460, the actual width at any locations on the spherical surface can be calculated from the width in pixels.

Second Embodiment

Hereafter, a second embodiment of the present invention will be described in detail with reference to FIGS. 26 to 30, which describes surface defects evaluation system and method for concave spherical optical components.

Surface defects evaluation system and method for concave spherical optical components described in the second embodiment of the present invention is similar to that for convex spherical optical components described in the first embodiment of the present invention. In order to avoid confusion and repetition, parts in FIGS. 26 to 30 which are relevant to parts in FIGS. 1 to 25 are indicated by the same reference numbers. Emphasis in the second embodiment is also put on parts different from the first embodiment.

Figure 26:
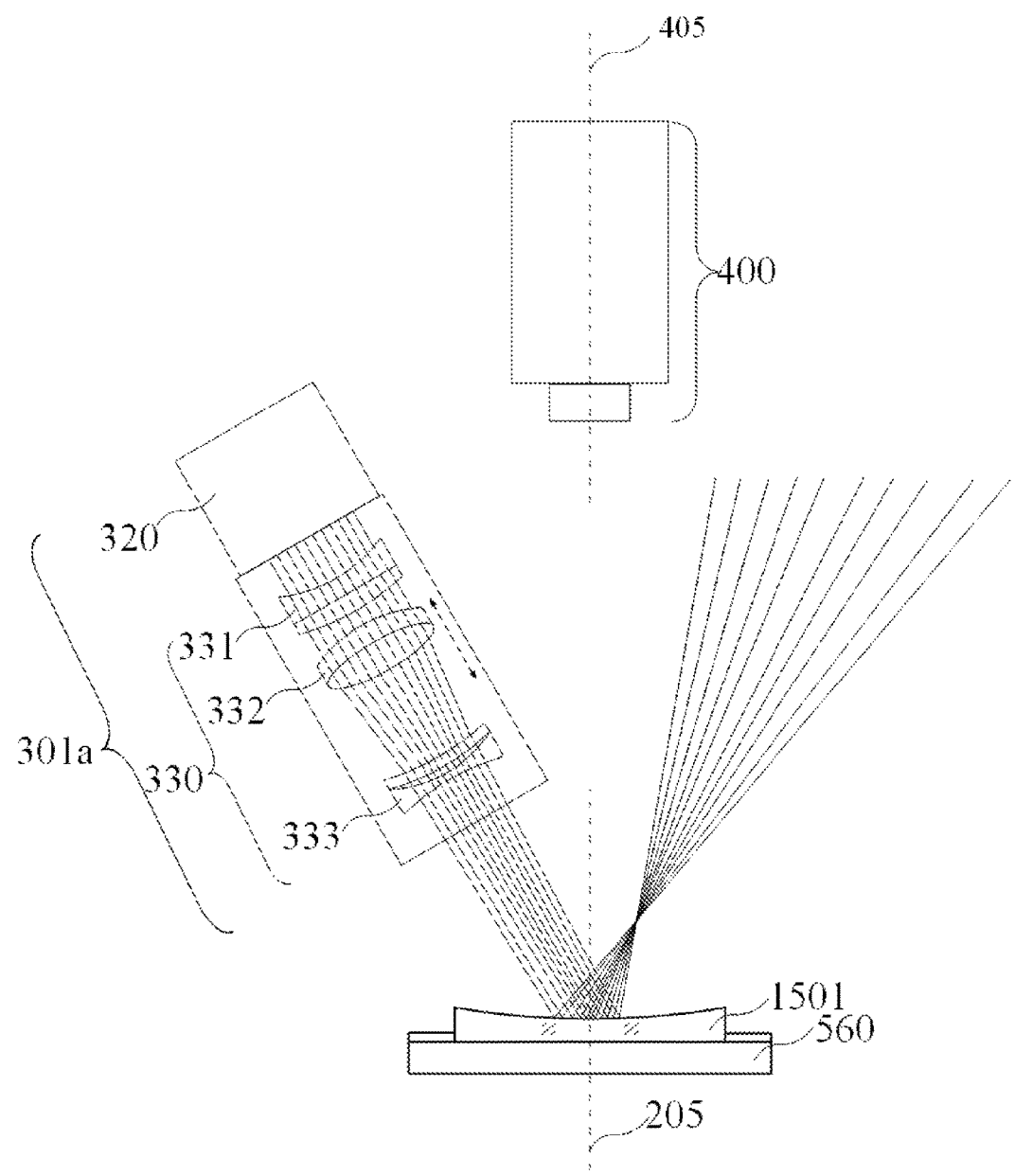
FIG. 26 illustrates a schematic diagram of the illumination light path in accordance with the second embodiment of the present invention.

FIG. 26 illustrates a schematic diagram of the illumination light path in accordance with the second embodiment of the present invention. The parallel light emitted by the uniform surface light source 320 passes through the lens group 330 and becomes convergent spherical wave with the aperture angle of $\theta_I$. The detailed process is as follows. The zoom lens group 332 is moved to the position in the lens group 330 calculated according to the curvature radius of the concave spherical optical component 1501. The parallel light emitted by the uniform surface light source 320 enters into the lens group 330 and passes through the front fixed lens group 331, the zoom lens group 332 and the rear zoom lens group 333 in turn. Finally it becomes convergent spherical wave with the aperture angle of $\theta_I$.

Figure 27:
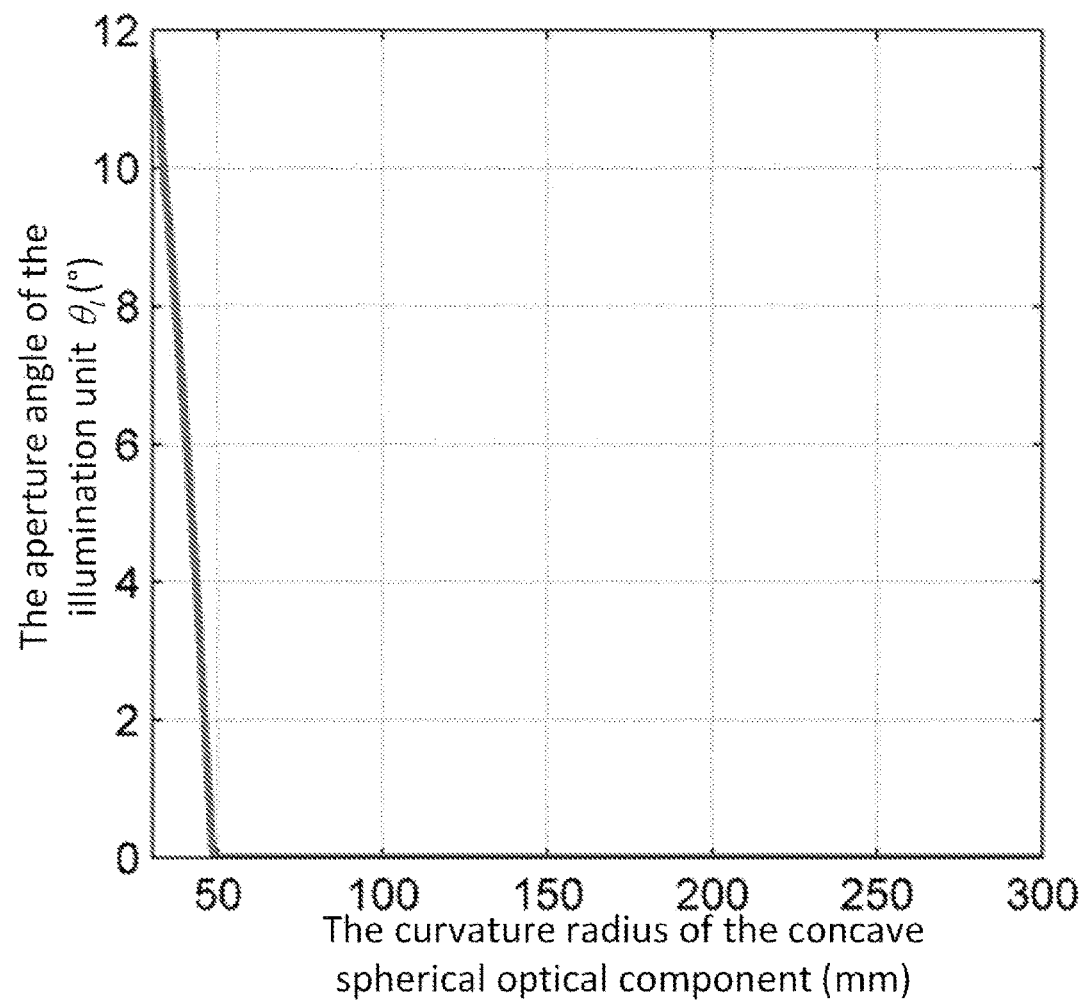
FIG. 27 illustrates a graph of the relationship between the curvature radius of the concave spherical optical component and the aperture angle of the illuminant in the case of the incident angle of 40° in accordance with FIG. 26.

FIG. 27 illustrates a graph of the relationship between the curvature radius of the concave spherical optical component and the aperture angle $\theta_I$ of the illuminant in the case of the incident angle γ of 40° in accordance with FIG. 26. It can be found that with the curvature radius increasing, the aperture angle $\theta_I$ decreases and the illumination range received by the surface also decreases. The aperture angle $\theta_I$ is less than or equal to 12°. Comparing FIG. 27 with FIG. 5, it can be seen that the aperture angle formed by illuminants' irradiating on the concave spherical optical component is smaller than that formed by illuminants' irradiating on the convex spherical optical component with the same curvature radius, the aperture angle decreases with the curvature radius increasing more sharply and the critical curvature radius corresponding with the aperture angle of 0° is smaller.

Figure 28:
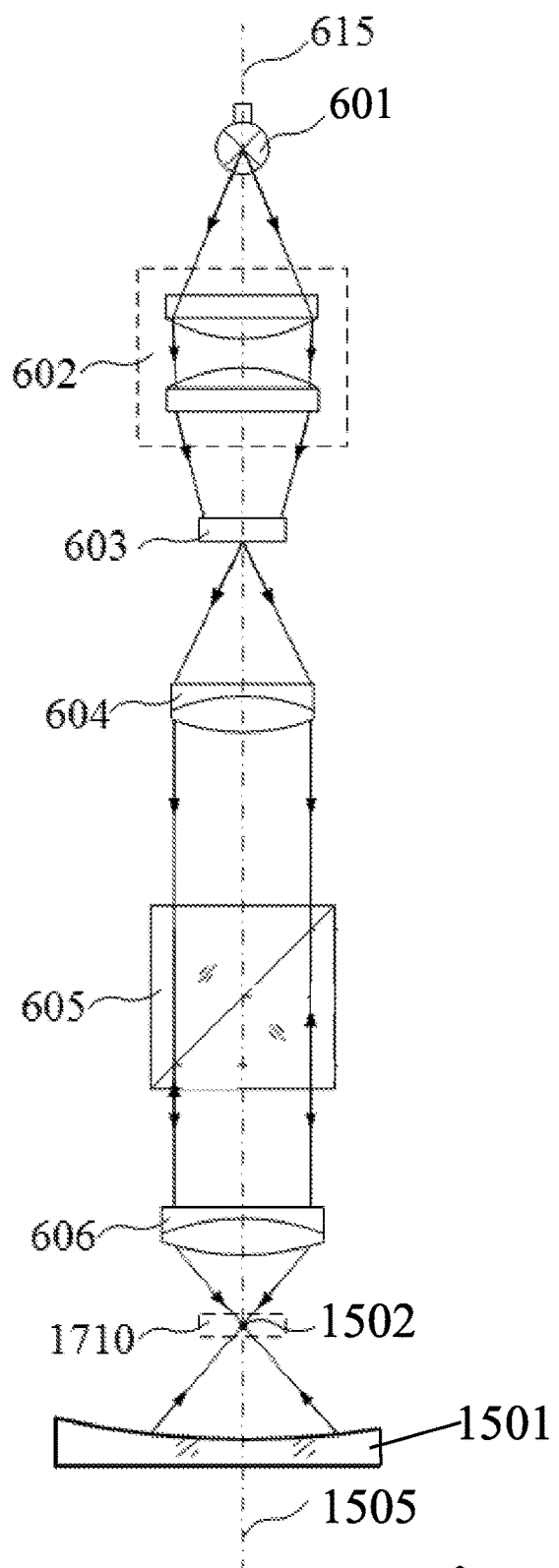
FIG. 28 illustrates a schematic diagram of the structure of the centering unit in accordance with the second embodiment of the present invention.
Figure 29A:
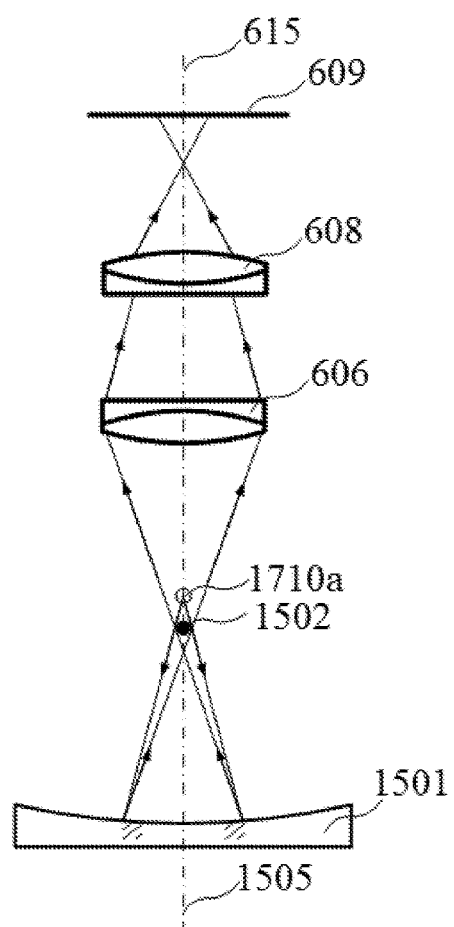
FIG. 29A illustrates a schematic diagram of the light path in the case of Z-direction deviation between the positions of the reticle image and the curvature center of the concave spherical optical component in accordance with FIG. 28.
Figure 29B:
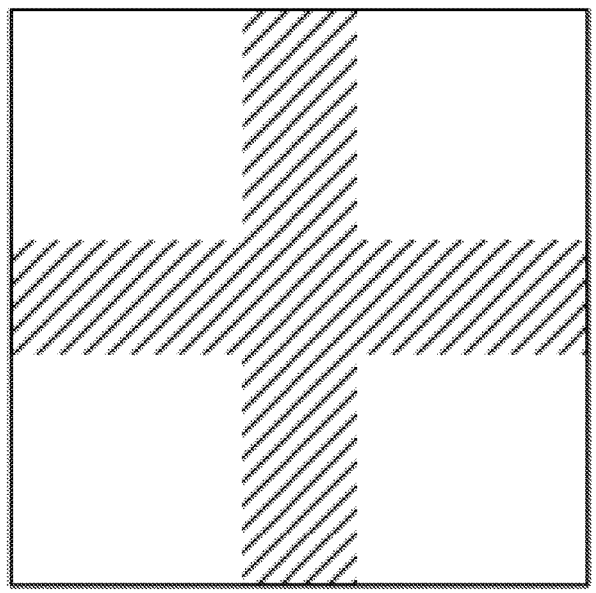
FIG. 29B illustrates an image of the crosshair captured by CCD in the case of Z-direction deviation between the positions of the reticle image and the curvature center of the concave spherical optical component in accordance with FIG. 28.
Figure 30A:
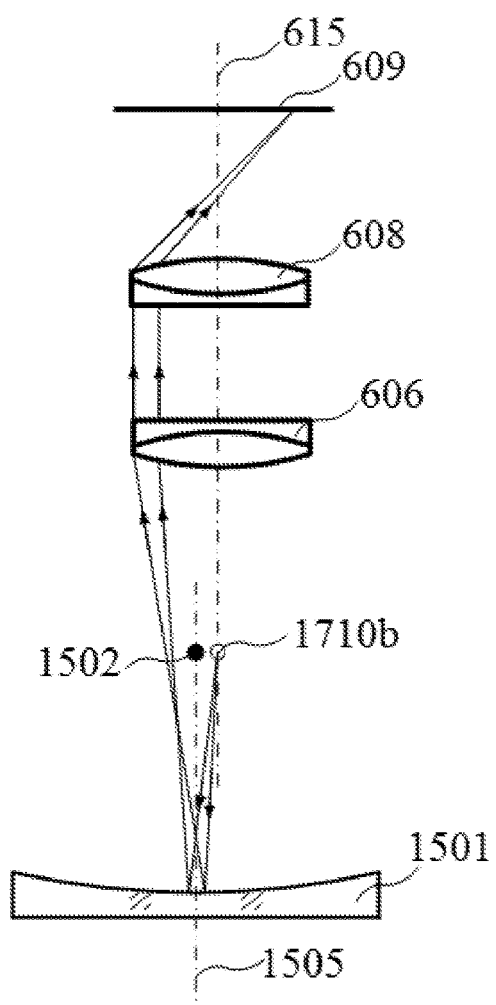
FIG. 30A illustrates a schematic diagram of the light path in the case of X-direction and Y-direction deviation between the positions of the reticle image and the curvature center of the concave spherical optical component in accordance with FIG. 28.
Figure 30B:
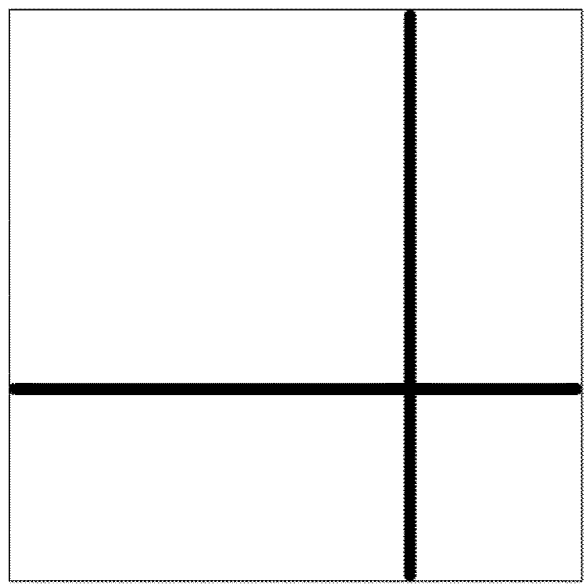
FIG. 30B illustrates an image of the crosshair captured by CCD in the case of X-direction and Y-direction deviation between the positions of the reticle image and the curvature center of the concave spherical optical component in accordance with FIG. 28.

FIG. 28 illustrates a schematic diagram of the structure of the centering unit 600 in accordance with the second embodiment of the present invention. The light path during the process of centering for the concave spherical optical component 1501 is similar to that during the process of centering for the convex spherical optical component 201. According to the position and clarity of the crosshair image, the relative position of the curvature center of the concave spherical optical component 1502 to the reticle image 1710 can be obtained as follows:

FIG. 29A illustrates a schematic diagram of the light path in the case of Z-direction deviation between the positions of the reticle image 1710a and the curvature center of the concave spherical optical component 1502 in accordance with FIG. 28. In this case, the reflected light beam doesn't coincide with the incident light beam so that the CCD 609 acquires fuzzy crosshair image, as is illustrated in FIG. 29B. Besides, FIG. 30A illustrates a schematic diagram of the light path in the case of X-direction and Y-direction deviation between the positions of the reticle image 1710b and the curvature center of the concave spherical optical component 1502 in accordance with FIG. 28. In this case, the optical axis of the concave spherical optical component 1502 doesn't coincide with the optical axis of the centering unit 615. The reflected light beam focuses on the CCD 609 so that the CCD 609 acquires sharp crosshair image which is not located in the center of the FOV, as is illustrated in FIG. 30B. Therefore according to the states of crosshair images on the CCD 609, the 3D-position of curvature center of the concave spherical optical component 1502 can be determined. The second embodiment of the present invention describes surface defects evaluation system and method for concave spherical optical components. The evaluation method for concave spherical optical components is the same as that described in the first embodiment. The illumination unit 300 and the centering unit 600 is different from those for convex spherical optical components due to the difference in surface shape.

Third Embodiment

Hereafter, a third embodiment of the present invention will be described in detail with reference to FIGS. 31 to 33, which describes surface defects evaluation system and method for the small-aperture spherical optical components. Similarly, in order to avoid confusion and repetition, parts in FIGS. 31 to 33 which are relevant to parts in FIGS. 1 to 25 are indicated by the same reference numbers. Emphasis in the third embodiment is also put on parts different from the first embodiment.

The small-aperture spherical optical component 1801 is characterized by that its aperture is smaller than the illumination aperture of the illumination unit 300 and the object field of view of the MS-DFI unit 400. Thus, the MS-DFI unit 400 needs to acquire only one sub-aperture located at the vertex of the spherical surface 1009 (as is illustrated in FIG. 15), which is the full-aperture image covering the whole surface of the small-aperture spherical optical components. Referring to FIGS. 31 to 33, surface defects evaluation system and method for small-aperture spherical optical components described in the third embodiment doesn't need the scan-path planning module and the image processing module 2000 only need to process one single sub-aperture. Correspondingly, the evaluation method 1900 is easier than that applied to the first and the second embodiment.

Figure 31:
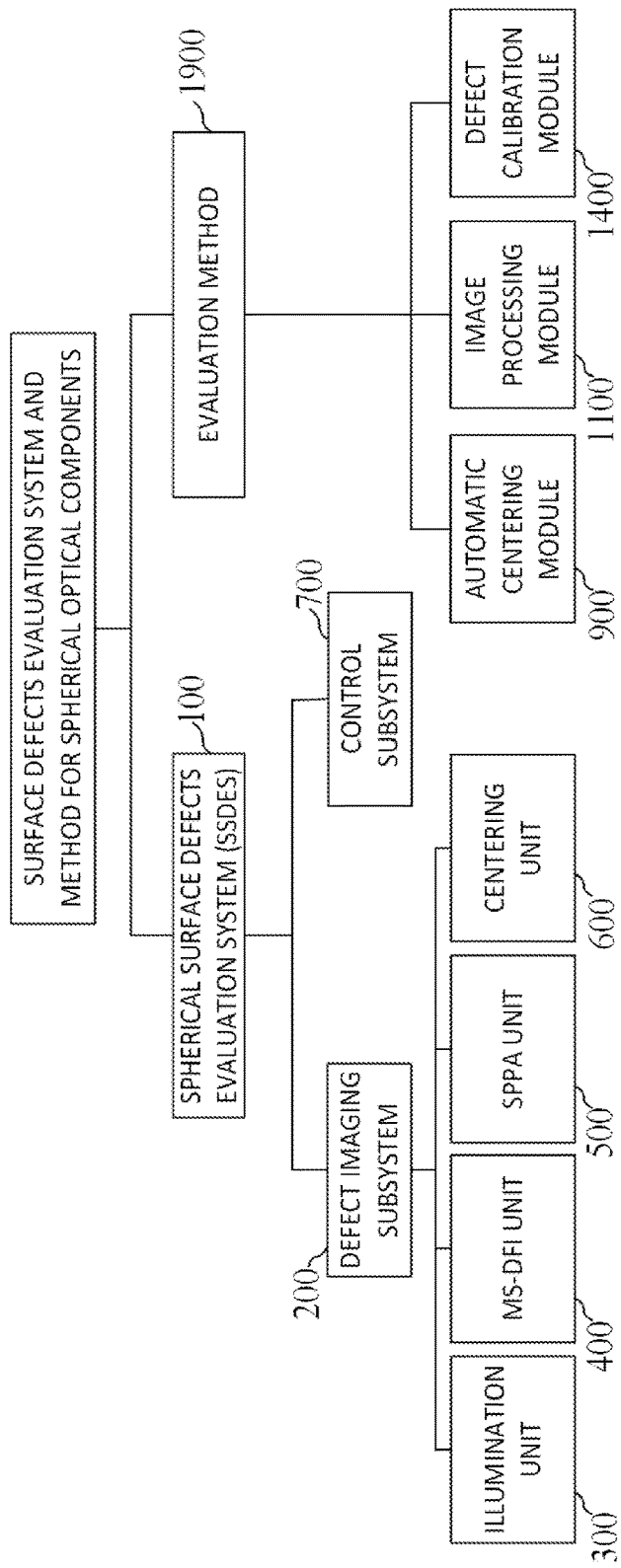
FIG. 31 illustrates a block diagram of surface defects evaluation system and method for spherical optical components in accordance with the third embodiment of the present invention.
Figure 32:
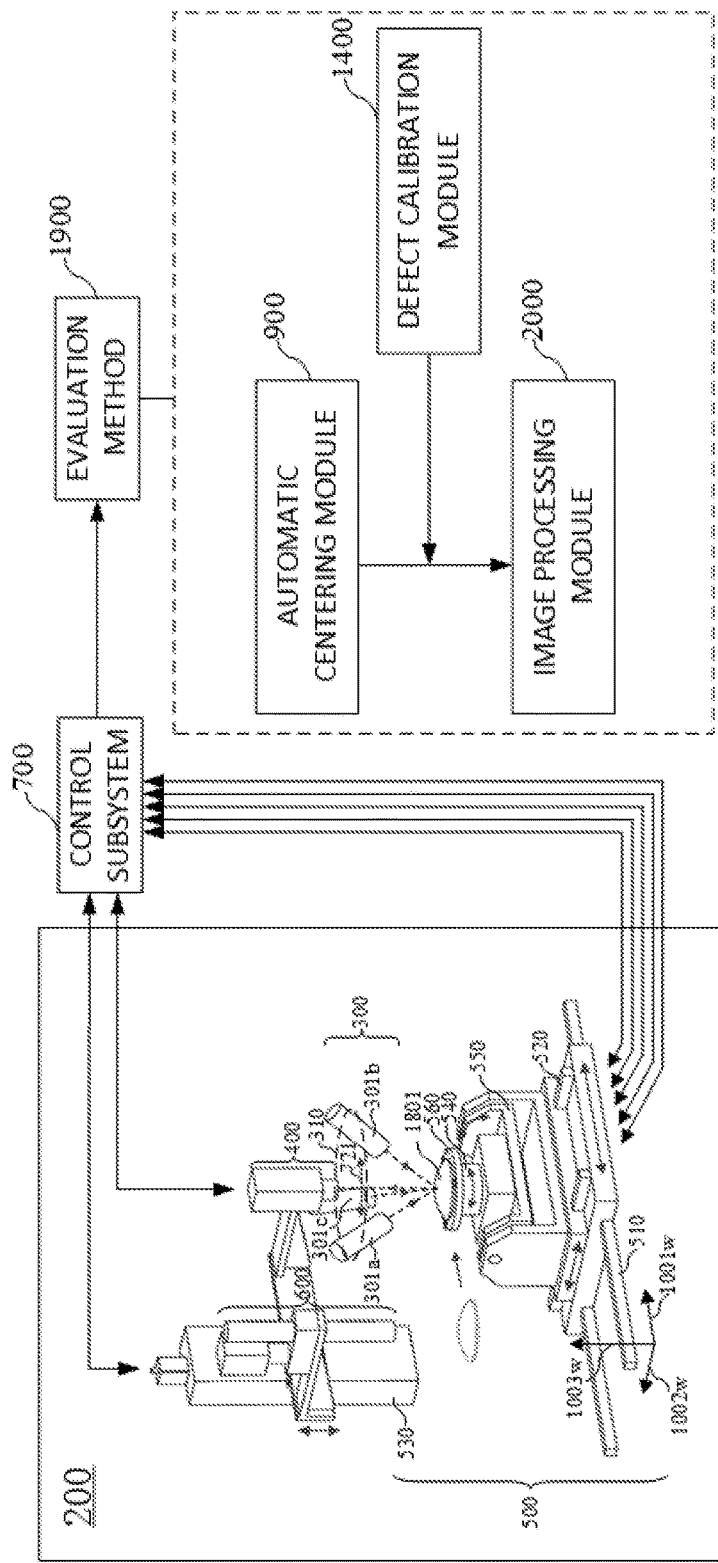
FIG. 32 illustrates a schematic diagram of all parts of surface defects evaluation system and method for spherical optical components in accordance with FIG. 31 in more detail.

FIG. 31 illustrates a block diagram of surface defects evaluation system and method for small-aperture spherical optical components in accordance with the third embodiment of the present invention. FIG. 32 illustrates a schematic diagram of all parts of surface defects evaluation system and method for small-aperture spherical optical components in accordance with FIG. 31 in more detail. Referring to FIGS. 31 and 32, the evaluation method 1900 comprises an automatic centering module 900, an image processing module 2000 and a defect calibration module 1400. The evaluation method 1900 comprises the following steps:

Step1. The implementation of automatic centering of the spherical optical component by the automatic centering module 900.

Step2. The obtainment of spherical surface defect information by the image processing module 2000 and the defect calibration module 1400.

Figure 33:
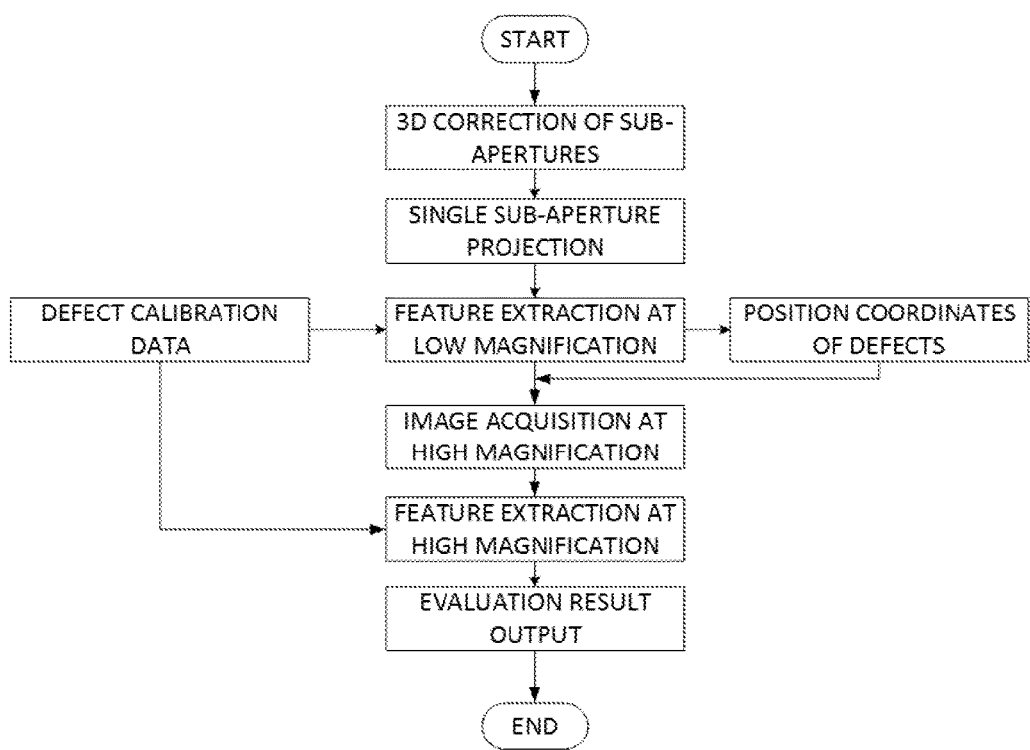
FIG. 33 illustrates a flowchart of the image processing module in accordance with FIG. 31.

FIG. 33 illustrates a flowchart of the image processing module 2000 in accordance with FIG. 31. Referring to FIG. 33, the obtainment of spherical surface defects information by the image processing module 2000 and the defect calibration module 1400 according to Step 2, comprises the following steps:

2-1. The imaging sub-aperture image is a 2D image, which is obtained when the surface of the small-aperture spherical optical component 1801 is imaged by the MS-DFI unit 400 in the image plane. 3D correction of sub-apertures should be conducted firstly to recover the information loss of surface defects of the small-aperture spherical optical component 1801 along the direction of optical axis during the optical imaging process.

2-2. For convenience of feature extraction, 3D sub-aperture images obtained after 3D correction of sub-apertures are projected onto a 2D plane with the single sub-aperture projection to obtain the single sub-aperture projective image.

2-3. Feature extraction at low magnification is conducted on the single sub-aperture projective image; then 3D sizes of defects is obtained with inverse-projection reconstruction; finally, actual sizes and positions of surface defects on the small-aperture spherical optical component 1801 are obtained taking advantages of the defect calibration data got with the calibration module 1400.

2-4. Defects are inspected at high magnification to guarantee the micron-scale inspection precision. First, the imaging magnification of the MS-DFI unit 400 is zoomed to high magnification; then, according to the positions obtained by Step 2-3, surface defects are moved to the center of the object field of view to acquire images at high magnification; Finally, feature extraction at high magnification is conducted and micron-scale evaluation results of defects are obtained taking advantages of the defect calibration data got with the calibration module 1400.

2-5. Evaluation results are output in the form of 3D panoramic preview of the spherical surface, electronic report and defect location map.

What is claimed is:

1. A spherical surface defects evaluation system (SSDES) comprising: a defect imaging subsystem and a control subsystem, wherein the defect imaging subsystem is adapted to acquire microscopic scattering dark-field images suitable for digital image processing, the control subsystem drives movements of various parts of the defect imaging subsystem, so as to acquire images of the inspected surface of the spherical optical component, the defect imaging subsystem comprises an illumination unit, a microscopic scattering dark-field imaging (MS-DFI) unit, a spatial position and posture adjustment (SPPA) unit and a centering unit, wherein the illumination unit is adapted to provide dark-field illumination for the microscopic scattering dark-field imaging unit of spherical surface, the MS-DFI unit is adapted to collect scatter light induced by the surface and image, the SPPA unit is adapted to achieve five-dimensional spatial position and attitude adjustment comprising three-dimensional translation, rotation and swing, easy to acquire sharp images at various locations on the surface of the spherical optical component, the centering unit is adapted to analyze position of a curvature center of the component, movement and adjustment of the illumination unit, the MS-DFI unit, the SPPA unit and the centering unit are driven by the control subsystem.

2. The SSDES according to claim 1, wherein the illumination unit comprises illuminants and an illuminant support bracket, wherein the illuminants comprise a uniform surface light source and a lens group with front fixed lens group, a zoom lens group and a rear fixed lens group installed in, the optical axis of the lens group intersects with the optical axis of the MS-DFI unit at an incident angle of γ ranging from 25 to 45 degrees.

3. The SSDES according to claim 2, wherein the illuminant support bracket comprises a top fixation board, a hollow shaft, a worm gear, a worm, a servo motor, a motor support, a plurality of bearings, a rotating cylindrical part and a plurality of illuminant fixation supports; wherein the illuminant is fixed on the illuminant support bracket which is fixed on the rotating cylindrical part, the rotating cylindrical part has flexible connections with the hollow shaft by the plurality of bearings, the worm gear, installed on the rotating cylindrical part has flexible connections with the worm, so as to achieve circular rotation by the drive of the servo motor, the servo motor is fixed on the top fixation board by the motor support and the hollow shaft is also fixed on the top fixation board, which is fixed on the Z-axis translation stage, the illuminant support bracket is applied to provide illumination for spherical surface defects in all directions.

4. The SSDES according to claim 3, wherein three illuminants are in annular and uniformly distributed at the angle interval of 120° by the illuminant fixation support on the rotating cylindrical part.

5. The SSDES according to claim 3, wherein the light path of the illumination unit is formed as follows, the zoom lens group is moved to the position in the lens group calculated according to the curvature radius of the spherical optical component, the parallel light emitted by the uniform surface light source enters into the lens group and passes through the front fixed lens group, the zoom lens group and the rear zoom lens group in turn, and finally becomes convergent spherical wave with the aperture angle of $\theta_i$.

6. The SSDES according to claim 1, wherein taking advantages of the induced scatter light by a principle that defects on the smooth surface modulate the incident light, the MS-DFI unit achieves microscopic dark-field imaging of defects and acquires dark-field images of defects, wherein the principle is: the incident light is incident onto the surface of the spherical optical component, if the spherical surface is smooth, the incident light, according to the law of reflection in geometrical optics, is reflected on the surface to form the reflected light, which is not capable of entering the MS-DFI unit; if there is defect on the surface of the spherical optical component, the incident light is scattered to form the scatter light, which is received by the MS-DFI unit and forms the dark-field image of defects.

7. The SSDES according to claim 1, wherein the SPPA unit comprises an X-axis translation stage, a Y-axis translation stage, a Z-axis translation stage, a rotation stage, a swing stage and a self-centering clamp, wherein the swing stage comprises an inner plate and a shell plate, the self-centering clamp has fixed connections with the rotation axis of the rotation stage and the base of the rotation stage is fixed on the inner plate of the swing stage, the inner plate has flexible connections with the shell plate so that the inner plate is capable of swinging by the shell plate, the sections of the inner plate and the shell plate are both in U-shape, the undersurface of the shell plate of the swing stage is fixed on the working surface of the Y-axis translation stage and the Y-axis translation stage is fixed on the working surface of the X-axis translation stage, the X-axis translation stage and the Z-axis translation stage are fixed on the same platform.

8. The SSDES according to claim 1, wherein the centering unit comprises a light source, a focusing lens group, a reticle, a collimation lens, a beam splitter, an objective, a plane reflector, an imaging lens and a CCD, wherein the light beam emitted by the light source passes through the focusing lens group and irradiates the reticle with a crosshair on, then, the light beam passes through the collimation lens, the beam splitter and the objective and irradiates on the spherical optical component, the light beam is reflected on the surface and the image of the crosshair on the reticle is indicated by the reticle image, the reflected light beam passes through the objective again and deflects at the beam splitter, subsequently, the reflected light beam is reflected by the plane reflector and passes through the imaging lens, finally, the light beam focuses on the CCD and the CCD acquires the image of the crosshair on the reticle.

9. The SSDES according to claim 1, wherein the control subsystem comprises a centering control module, an illumination control module, a five-stage translation control module and an image acquisition control module, the centering control module comprises a centering image acquisition unit and a four-stage translation control unit, the centering image acquisition unit is applied to control the CCD of the centering unit to acquire the image of the crosshair and the four-stage translation control unit is applied to control the movement of the X-axis translation stage, the Y-axis translation stage and the Z-axis translation stage and the rotation of the rotation stage during the process of centering, the illumination control module comprises an illumination rotating control unit and an illuminant zoom control unit, the illumination rotating control unit is applied to control the rotation of the illuminant support bracket of the illumination unit and the illuminant zoom control unit is applied to control the movement of the zoom lens group to change the aperture angle $\theta_l$ of the emitted convergent spherical wave, the five-stage translation control module is applied to control the movement of the X-axis translation stage, the Y-axis translation stage and the Z-axis translation stage, the rotation of the rotation stage and the swing of the swing stage during the process of inspection, the image acquisition control module comprises a sub-aperture image acquisition unit and a microscope zoom control unit, the sub-aperture image acquisition unit is applied to control the MS-DFI unit to acquire sub-aperture images and the microscope zoom control unit is applied to change the image magnification of the MS-DFI unit.

10. The SSDES according to claim 1, comprising: an automatic centering module, a scan-path planning module, an image processing module and a defect calibration module, the automatic centering module is adapted to automatic centering of the spherical surface, achieving accurate measurement of the curvature radius and axial consistency alignment between the rotation axis and the optical axis of the spherical optical component, the scan-path planning module is adapted to plan the optimal scan-path for the spherical surface, the image processing module is adapted to achieve spherical surface detects inspection with high precision, the detect calibration module is adapted to establish the relationship between pixels and actual size in sub-aperture images at any locations on the spherical surface so as to obtain an actual size of defects, the evaluation method comprises steps of:

step 1, automatic centering the spherical optical component by the automatic centering module;

step 2, the completing of optimal scan-path planning and full-aperture scanning for the spherical optical component by the scan-path planning module;

step 3, processing the sub-aperture images to obtain spherical surface defect information by the image processing module and the defect calibration module.

11. The evaluation method according to claim 10, wherein the step (1) of automatic centering the spherical surface by the automatic centering module, comprises steps of:

(1-1) initializing the centering unit;

(1-2) moving the spherical optical component to the initial position, wherein the optical axis of the spherical optical component coincides with the optical axis of the centering unit approximately;

(1-3) controlling the Z-axis translation stage to scan along Z-direction to find the sharpest crosshair image by use of image entropy clarity evaluation function;

(1-4) judging whether the crosshair image is the surface image or the center image comprising:

moving the X-axis translation stage and Y-axis translation stage slighted to observe whether the crosshair image in the field of view[7] (FOV) is moved with the movement of translation stages or not; wherein if the crosshair image is moved with the movement of stages, it is the center image of the spherical optical component located at the curvature center of the spherical optical component and then jump to Step 1-5, otherwise, it is the surface image of the spherical optical component located on the surface of the spherical optical component and then jump to Step 1-9;

(1-5) moving the crosshair image to the center of FOV by the X-axis translation stage and the Y-axis translation stage, until the optical axis of the spherical optical component coincides with the optical axis of the centering unit;

(1-6) finding the position of the rotation axis by rotation measurement in optical alignment as follows:

the spherical optical component is capable of rotating around the rotation axis of the rotation stage under the self-centering clamp, every 30° rotation of the rotation stage, CCD acquires a crosshair image, the positions of the crosshair images in the FOV of CCD vary with different rotation angles, the trajectory formed by the center of the crosshair is close to a circle, the center of which is the position of the rotation axis;

(1-7) obtaining the trajectory center by a least square circle fitting method and the max deviation between the trajectory center and the crosshair center is calculated;

(1-8) judging whether the max deviation is lower than the max permissible error, if the max deviation is lower than the max permissible error, the axial consistency alignment is considered completed, otherwise, the optical axis of the spherical optical component is not coincident with the rotation axis, therefore the center of the crosshair image is moved to the fitting trajectory center by adjusting the self-centering clamp and then jump to Step 1-5;

(1-9) moving the Z-axis translation stage to image at theoretical curvature center obtained by initialization, the Z-axis translation stage is controlled to scan along Z-direction to find the sharpest crosshair image and then jump to Step 1-5, at the same time, Z-direction displacement from the position of the surface image to the position of the center image is recorded to get the real curvature radius of the spherical optical component, which is the displacement of the Z-axis translation stage.

12. The evaluation method according to claim 10, wherein the completion of optimal scan-path planning and full-aperture scanning of the spherical optical component by the scan-path planning module according to Step2 comprises steps of:

(2-1) with the fiducial position obtained in the process of axial consistency alignment in Step 1, moving the spherical optical component by the SSPA unit below the MS-DFI unit, then acquiring the image of the sub-aperture located on the vertex of the spherical optical component by the MS-DFI unit, wherein for the convenience of the following statement, spherical coordinate system $X_s Y_s Z_s$ is defined here, where the origin of spherical coordinate system $O_s$ is located in the curvature center of the spherical optical component and the z-axis of spherical coordinate system $Z_s$ passes through the vertex of the spherical optical component, to achieve the full-aperture sampling, two-dimension movements along the meridian and parallel scanning trajectory is required, combining the swing around $X_s$ and the rotation around $Z_s$;

(2-2) driving the spherical optical component to swing around $X_s$ with swing angle $\beta_1$, sub-aperture images are acquired on meridian; then rotating around $Z_s$ with rotation angle $\alpha_1$ to acquire sub-aperture images on the parallel;

(2-3) every time after the rotation around $Z_s$ with the same rotation angle $\alpha_1$, one sub-aperture image is acquired so that multiple sub-aperture images on the parallel are obtained;

(2-4) after the completion of sub-aperture image acquisition on the parallel, driving the spherical optical component to swing around $X_s$ again with swing angle $\beta_2$, in such a manner that one sub-aperture is acquired on meridian;

(2-5) every time after the rotation around $Z_s$ with the same rotation angle $\alpha_2$, acquiring one sub-aperture image, to obtain multiple sub-aperture images on the parallel, wherein full-aperture sampling is finished with several times repetition of such a process that the spherical optical component is driven to swing around $X_s$ to acquire multiple sub-aperture images on next parallel after the completion of sub-aperture image acquisition on this parallel.

13. The evaluation method according to claim 10, wherein the completion of optimal scan-path planning and full-aperture scanning of the spherical optical component by the scan-path planning module according to Step 2 is characterized by that the spherical sub-aperture plan model is established firstly, in this model, sub-aperture A and sub-aperture B are two adjacent sub-apertures on meridian C, sub-aperture Aa is adjacent to sub-aperture A on the parallel D1 where sub-aperture A is located, similarly, sub-aperture Bb is adjacent to sub-aperture B on the parallel D2 where sub-aperture B is located, besides, the bottom intersection of sub-aperture A and sub-aperture Aa is indicated by $P_{cd}$, the top intersection of sub-aperture B and sub-aperture Bb is indicated by $P_{cu}$, so the sufficient conditions for the realization of sub-aperture no-leak inspection is that the arc length $\overarc{P_{cu}O_T}$ is less than or equal to the arc length $\overarc{P_{cd}O_T}$, under such a constraint, planning result can be solved and obtained by establishing the relationship between swing angle $\beta_1$, swing angle $\beta_2$ and rotation angle $\alpha_1$, rotation angle $\alpha_2$, the solution procedure of swing angle $\beta_1$, swing angle $\beta_2$, rotation angle $\alpha_1$ and rotation angle $\alpha_2$ is as follows:

① validating relevant parameters about the spherical optical component, including the curvature radius, aperture of the spherical optical component and the size of the object field of view of the MS-DH unit;

② specifying the initial value of swing angle $\beta_1$ and swing angle $\beta_2$ according to the above three parameters, after that, calculate the value of rotation angle $\alpha_1$ and rotation angle $\alpha_2$ according to the overlapping area between adjacent sub-apertures on one parallel, then, figure out arc length $\overarc{P_{cu}O_T}$ and arc length $\overarc{P_{cd}O_T}$;

③ comparing arc length $\overarc{P_{cu}O_T}$ and arc length $\overarc{P_{cd}O_T}$ to determine whether the given initial value of swing angle $\beta_2$ is appropriate or not, wherein If $\overarc{P_{cu}O_T} > \overarc{P_{cd}O_T}$, reduce the value of swing angle $\beta_2$ by 5% and go back to Step ②, otherwise, sub-aperture plan for covering the entire spherical surface is finished.

14. The evaluation method according to claim 10, wherein the obtainment of spherical surface defects information by the image processing module and the defect calibration module according to Step 3, comprises steps of:

(3-1) obtaining the imaging sub-aperture image is a 2D image_when the surface of the spherical optical component is imaged by the MS-DFI unit in the image plane, wherein due to the information loss along the direction of optical axis during the optical imaging process, 3D correction of sub-apertures should be conducted firstly to recover the information loss of surface defects of the spherical optical component along the direction of optical axis during the optical imaging process 3D correction of sub-apertures means that the imaging process of the MS-DFI unit is simplified to be a pin-hole model and imaging sub-aperture images are transformed into 3D sub-aperture images with geometrical relationship;

(3-2) for convenience of feature extraction, obtaining 3D sub-aperture images after 3D correction of sub-apertures are projected onto a 2D plane with full-aperture projection to obtain the full-aperture projective image;

(3-3) conducting feature extraction at low magnification on the full-aperture projective image; then obtaining 3D sizes of defects with inverse-projection reconstruction; finally, obtaining actual sizes and positions of surface defects on the spherical optical component taking advantages of the defect calibration data got with the calibration module;

(3-4) inspecting defects at high magnification to guarantee the micron-scale inspection precision, wherein first, the imaging magnification of the MS-DFI unit is zoomed to high magnification; then, according to the positions obtained by Step 3-3, surface defects are moved to the center of the object field of view to acquire images at high magnification; and Finally, feature extraction at high magnification is conducted and micron-scale evaluation results of defects are obtained taking advantages of the defect calibration data got with the calibration module;

(3-5) outputting evaluation results in the form of a 3D panoramic preview of the spherical surface, an electronic report and a defect location map.

15. The evaluation method according to claim 14, wherein according to Step 3-1, imaging sub-aperture images are obtained when the surface of the spherical optical component is imaged by the MS-DFI unit in the image plane, the detailed description is:

(3-1-1) according to the optimal scan-path planned by the scan-path planning module in Step 2, moving one point p on the surface of the spherical optical component to the point p' by the SPPA unit;

(3-1-2) acquiring sub-apertures at low magnification by the MS-DFI unit, wherein Point p' is imaged to be image point p" in the imaging sub-aperture image by the MS-DFI unit;

(3-1-3) during the process of digital image acquisition, transforming the image-plane coordinate system $X_cY_c$ into the image coordinate system $X_iY_i$ to obtain the imaging sub-aperture image, wherein X-axis $X_c$ and y-axis $Y_c$ compose the image-plane coordinate system $X_cY_c$, whose origin $O_c$ is located at the intersection of the optical axis of the MS-DFI unit and the imaging sub-aperture image, X-axis $X_i$ and y-axis $Y_i$ compose the image coordinate system $X_iY_i$ coordinate system, whose origin $O_i$ is located at the top left corner of the digital image.

16. The evaluation method according to claim 14, wherein according to Step 3-2, obtaining the full-aperture projective image comprises steps of:

(3-2-1) transforming 3D sub-aperture images into spherical sub-aperture images by global coordinate transformation;

(3-2-2) projecting spherical sub-aperture images vertically onto the plane to obtain projective sub-aperture images;

(3-2-3) stitching projective sub-aperture images and extracting sizes and positions of defects in the plane, in such a manner that recise inspection for surface defects of the spherical optical component is achieved by inverse-projection reconstruction.

17. The evaluation method according to claim 16, wherein the way of direct stitching for parallel circle and annulus stitching for meridian circle is used for image stitching of projective sub-aperture images, wherein the process of image stitching of projective sub-aperture images comprises steps of:

(step ①) denoising projective sub-aperture images to remove the effect of background noise on stitching accuracy;

(step ②) after denoising, carrying out image registration according to overlapping area on adjacent projective sub-aperture images on the same parallel circle;

(step ③) stitching adjacent projective sub-aperture images after registration on the same parallel circle to obtain the annulus image of one parallel circle;

(step ④) extracting the minimum annulus image containing all overlapping areas;

(step ⑤) extracting the image registration points of the minimum annulus image to acquire the best registration location, so that the image stitching of projective sub-aperture images is finished.

18. The evaluation method according to claim 14, wherein according to Step 3-3, feature extraction at low magnification is conducted on the full-aperture projective image; then, 3D sizes of defects is obtained with inverse-projection reconstruction; finally, actual sizes and positions of surface defects of the spherical optical component are obtained taking advantages of the defect calibration data got with the defect calibration module, wherein detailed description is:

(3-3-1) extract features of the 2D full-aperture image after image stitching of projective sub-aperture images to obtain sizes and positions of defects;

(3-3-2) obtain 3D sizes and positions in pixels of surface defects of the spherical optical component by inverse-projection reconstruction;

(3-3-3) taking advantages of the defect calibration data got with the defect calibration module, convert 3D sizes and positions in pixels to actual sizes and positions.

19. The evaluation method according to claim 14, wherein the defect calibration data according to Step (3-3) and Step (3-4) comprises defect length calibration data and defect width calibration data, the process of defect length calibration is to establish the relationship between actual lengths of line segments at any locations on the spherical surface and corresponding pixels in spherical sub-aperture images, wherein the defect length calibration data is obtained by steps of:

firstly, taking a standard line segment $d_l$ in the object plane and a length thereof is measured by a standard measuring instrument, the standard line segment $d_l$ is imaged by the MS-DFI unit and an image $d_p$ of the standard line is obtained in the imaging sub-aperture image;

then, transforming this imaging sub-aperture image into a 3D sub-aperture image by 3D correction, in which the spherical image of standard line segment $d_l$, namely a short arc $d_c$ on the spherical surface is be obtained, wherein the size of $d_c$ is quantified in pixels and its corresponding arc angle $d_\theta$ is obtained, since the curvature radius R of the spherical optical component is determined accurately during the process of centering, the corresponding actual size of $d_c$ is be deduced by $d=Rd_\theta$, by establishing the relationship between $d_c$ and d, the relationship between the pixels in the 3D sub-aperture image and the actual size is calibrated, namely the calibration coefficient $k=d/d_c$, if substituting the equation $d=Rd_\theta$, $k=Rd_\theta/d_c$ is obtained, continuing to substitute the equation $d_c=R_{pixel}d_\theta$, finally calibration coefficient is reduced by $k=R/R_{pixel}$, where $R_{pixel}$ is the curvature radius in pixels of the 3D spherical surface image, called pixel curvature radius for short, to extract the length of surface defects on one spherical optical component, feature extraction is firstly implemented to get each pixel's position coordinates of defects, then the continuous defects are discretized into a plurality of line segments described by a series of line equations $l_i$: $y_i = k_i x_i + b_i$ based on position coordinates, where $i=1, 2, 3 \ldots n$, after the process of inverse-projection reconstruction for each line segment, the corresponding arc $C_i$ of line segment $l_i$ on the spherical surface with the curvature radius $R_{pixel}$ is obtained, and the length of defects in pixels can be figured out with the surface integral equation:

$$L_{pixel} = \sum_{i=1}^{n} \left( \int_{C_i} ds \right)$$

wherein ds refers to the curve differential element, after substituting the calibration coefficient k, the actual length of defects is be obtained by:

$$L_{real} = \sum_{i=1}^{n} k_i \left( \int_{C_i} ds \right).$$

20. The evaluation method according to claim 19, wherein the defect width calibration data is obtained by a method comprising steps of:

firstly, in the 3D coordinate system, taking a standard line segment in the object plane and measuring an actual width of a standard line segment by a standard measuring instruments, wherein the standard line segment is imaged by the MS-DFI unit and an image of the standard line segment is obtained in the imaging sub-aperture image;

then, transforming the imaging sub-aperture image into a 3D sub-aperture image by 3D correction, in which the spherical image of the standard line segment is obtained, wherein for the spherical image, the arc length in pixels along width direction is the width of defects in pixels, since the defects are located in the center of FOV during the process of image acquisition at high magnification, information loss along the direction of the optical axis is ignored, thus, the actual width of defects is equal to that of the standard line segment;

finally, performing piecewise fitting for the corresponding discrete points of actual width and width in pixels of defects to obtain the best fitting curve, which is as the calibration transfer function (CTF), with the CTF, and calculating the actual width at any locations on the spherical surface from the width in pixels.

* * * * *